(12) United States Patent
Bilodeau et al.

(10) Patent No.: US 6,958,340 B2
(45) Date of Patent: Oct. 25, 2005

(54) TYROSINE KINASE INHIBITORS

(75) Inventors: Mark T. Bilodeau, Lansdale, PA (US); Peter J. Manley, Harleysville, PA (US); Adrienne Balitza, Philadelphia, PA (US); George D. Hartman, Lansdale, PA (US); Leonard Rodman, New York, NY (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/485,170

(22) PCT Filed: Jul. 26, 2002

(86) PCT No.: PCT/US02/23764

§ 371 (c)(1),
(2), (4) Date: Jan. 29, 2004

(87) PCT Pub. No.: WO03/011836

PCT Pub. Date: Feb. 13, 2003

(65) Prior Publication Data

US 2004/0220201 A1 Nov. 4, 2004

Related U.S. Application Data

(60) Provisional application No. 60/309,400, filed on Aug. 1, 2001.

(51) Int. Cl.$^7$ .................... C07D 403/04; A61K 31/506; A61P 35/00
(52) U.S. Cl. ................... 514/256; 514/272; 514/275; 544/324; 544/326
(58) Field of Search ................... 544/324, 326; 514/256, 272, 275

(56) References Cited

U.S. PATENT DOCUMENTS

| 6,200,977 B1 | 3/2001 | Cushing et al. |
| 6,410,726 B1 | 6/2002 | Powers |

FOREIGN PATENT DOCUMENTS

| WO | WO-01/85700 A2 * | 11/2001 |
| WO | WO 02/102783 | 12/2002 |
| WO | WO 03/011837 | 2/2003 |
| WO | WO 03/011838 | 2/2003 |

OTHER PUBLICATIONS

West, Anthony R., Solid State Chemistry and its Applications, Wiley, New York, 1988, pp. 358 & 365.*
Hasan et al. Expert Opin. Bio. Ther. 1(4): 703–718, 2001.*
Pergram et al. Semin. Oncol. 3 Suppl 11: 29–37, 2002.*
J. Rak et al. Cancer Research, 55:4575–4580, 1995.
G. Gasparini and A.L. Harris, J. Clin. Oncol., 1995, 13:765–782.
M. Toi et al., Japan. J. Cancer Res., 1994, 85:1045–1049.
A.J. Dickinson et al., Br. J. Urol., 1994, 74:762–766.
L.M. Ellis et al., Surgery, 1996, 120(5):871–878.
J.K. Williams et al., Am. J. Surg., 1994, 168:373–380.
A. Amirkhosravi et al., Platelets, 10:285–292 (1999).
S.P. Gunningham, et al., Can. Research, 61: 3206–3211 (2001).
A. Giatromanolaki et al., J. Pathol. 2001; 194:101–108.
Michael Detmar, J. Dermatological Sci., 24 Suppl. 1, S78–S84 (2000).
Hasegawa et al., Skeletal Radiol., vol. 28, pp. 41–45, 1999.
Brockelsby et al., Laboratory Investigation 79:1101–1111 (Sep. 1999).
Paul et al., Nature Med 7:222–227 (2001).
Matsuyama et al., J. Neurol. Sci. 186:75–79 (2001).
van der Flier et al., J. Infectious Diseases, 183:149–153 (2001).
Stephen K. Smith, Trends in Endocrinology & Metabolism, vol. 12, No. 4, pp. 147–151, May/Jun. 2001.
Levis et al., Blood, vol. 98, No. 3, pp. 885–887 (2001).
Rajesh K. Jain, Nature Medicine, vol. 7, No. 9, pp. 987–989 (Sep. 2001).
Giulio Jori, Lasers Med. Sci., 1990; 5: 115–120.
Chuannong Zhou, J. Photochem. and Photobiol. 1989; 3: 299–318.
Hendrich et al., Knee Surg Sports Traumatol Arthroscopy 5: 58–63 (1997).
Hall et al., Am J Hum Genet 61:785–789, 1997.
Li et al., Gene Therapy, 1998; 5:1105–13.
Fathallah–Shaykh et al., J Immunol 2000; 164:217–222.
Dougherty et al., J. Natl. Cancer Inst., 1998, 90(12): 889–905.
Van Bruggen et al., J. Clin. Invest,. 104:1613–1620 (1999).
Gerber et al., Nature Medicine, vol. 5, No. 6, pp. 623–628, 1999.
David A. Greenberg, Drug News Perspect 11(5):265–270 (1998).
Nakagawa et al., FEBS Let. 473:161–164 (2000).
Peter Traxler, Exp. Opin. Ther. Patents 8 (12) 1599–1625(1998).
Peter M. Traxler, Exp. Opin. Ther. Patents 7(6) 571–588 (1997).
Joseph V. Simone, Cecil Textbook of Medicine 20th Edition, vol. 1, pp. 1004–1010 (1996).
Lawrence et al., Pub Med Abstract, vol. 77(2), pp. 81–114 (1998).

* cited by examiner

*Primary Examiner*—Venkataraman Balasubramanian
(74) *Attorney, Agent, or Firm*—Matthew A. Leff; Mark R. Daniel

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

12 Claims, No Drawings

TYROSINE KINASE INHIBITORS

This application is a 371 of PCT/US02/23764 filed 26 Jul. 2002, which claims benefit of U.S. Provisional Application No. 60/309,400 filed 1 Aug. 2001.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases play critical roles in signal transduction for a number of cell functions. Though the exact mechanisms of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene*, 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895–898, 1995). One such receptor-type tyrsoine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine & Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts, hydrates or stereoisomers thereof:

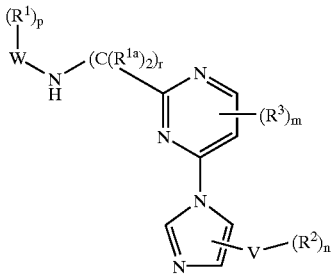

I

DETAILED DESCRIPTION OF THE INVENTION

The compounds of this invention are useful in the inhibition of kinases and are illustrated by a compound of Formula I:

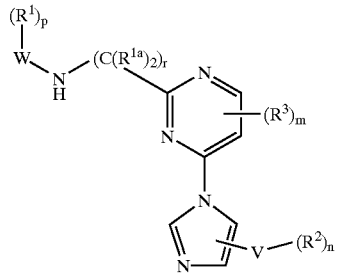

I wherein
$R^{1a}$ is selected from:
  (1) H,
  (2) unsubstituted or substituted $C_1$–$C_{10}$ alkyl,
  (3) $OR^8$, and
  (4) $N(R^8)_2$;
$R^1$ is independently selected from:
  (1) H,
  (2) unsubstituted or substituted $C_1$–$C_{10}$ alkyl,
  (3) unsubstituted or substituted $C_3$–$C_{10}$ cycloalkyl,
  (4) unsubstituted or substituted aryl,
  (5) unsubstituted or substituted heterocycle,
  (6) halo,
  (7) $CF_3$,
  (8) —$(CH_2)_rR^9C(O)R^8$,
  (9) —$C(O)R^9$,
  (10) —$(CH_2)_tOR^8$,
  (11) unsubstituted or substituted $C_2$–$C_6$ alkenyl,
  (12) unsubstituted or substituted $C_2$–$C_6$ alkynyl,
  (13) CN,
  (14) $(CH_2)_tNR^7R^8$,
  (15) —$(CH_2)_tC(O)NR^7R^8$,
  (16) —$C(O)OR^8$,
  (17) —$(CH_2)_tS(O)_q(CH_2)_tNR^7R^8$, and
  (18) oxido;
$R^2$ is independently selected from:
  (1) H,
  (2) unsubstituted or substituted $C_1$–$C_{10}$ alkyl,
  (3) unsubstituted or substituted $C_3$–$C_{10}$ cycloalkyl,
  (4) unsubstituted or substituted aryl,
  (5) unsubstituted or substituted heterocycle,
  (6) halo,
  (7) $CF_3$,
  (8) —$(CH_2)_rR^9C(O)R^8$,
  (9) —$C(O)R^9$,
  (10) —$(CH_2)_tOR^8$,
  (11) unsubstituted or substituted $C_2$–$C_6$ alkenyl,
  (12) unsubstituted or substituted $C_2$–$C_6$ alkynyl,
  (13) CN,
  (14) $(CH_2)_tNR^7R^8$,
  (15) —$(CH_2)_tC(O)NR^7R^8$,
  (16) —$C(O)OR^8$,
  (17) —$(CH_2)_tS(O)_q(CH_2)_tNR^7R^8$, and
  (18) oxido;

$R^3$ is independently selected from:
  (1) H,
  (2) unsubstituted or substituted $C_1$–$C_{10}$ alkyl,
  (3) unsubstituted or substituted aralkyl,
  (4) unsubstituted or substituted aryl,
  (5) CN,
  (6) halo,
  (7) $N(R^8)_2$, and
  (8) —$(CH_2)_tOR^8$;
$R^7$ is independently selected from:
  1) H,
  2) unsubstituted or substituted $C_1$–$C_{10}$ alkyl, and
  3) unsubstituted or substituted aralkyl;
$R^8$ is independently selected from:
  (1) H,
  (2) unsubstituted or substituted $C_1$–$C_{10}$ alkyl,
  (3) unsubstituted or substituted aryl,
  (4) unsubstituted or substituted heterocycle,
  (5) unsubstituted or substituted $C_3$–$C_{10}$ cycloalkyl, and
  (6) unsubstituted or substituted aralkyl;
$R^7$ and $R^8$, when attached to the same nitrogen atom, may be joined to form a 5 to 7-membered heterocycle containing, in addition to the nitrogen, one or two more heteroatoms, selected from N, O, or S, said heterocycle being optionally substituted with one to three $R^2$ substituents;
$R^9$ is independently selected from:
  1) unsubstituted or substituted heterocycle,
  2) unsubstituted or substituted $C_1$–$C_6$ alkyl, and
  3) unsubstituted or substituted aryl;
V is selected from:
  1) a bond,
  2) aryl, and
  3) heterocycle;
W is selected from:
  (1) aryl, and
  (2) heterocycle;
m is 0, 1, 2, or 3;
n is 0, 1, 2, 3, 4, 5, or 6;
p is 0, 1, 2, 3, or 4;
q is independently 0, 1 or 2;
t is independently 0 to 6;
or a pharmaceutically acceptable salt, hydrate or stereoisomer thereof.

Another embodiment of the instant invention is illustrated by a compound of Formula I:

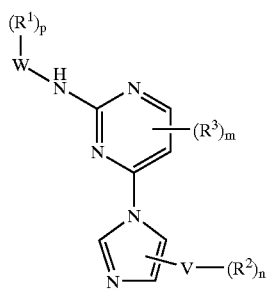

I wherein
$R^{1a}$ is selected from:
  (1) H,
  (2) unsubstituted or substituted $C_1$–$C_{10}$ alkyl, and
  (3) $OR^8$;
$R^1$ is independently selected from:
  (1) H,
  (2) unsubstituted or substituted $C_1$–$C_{10}$ alkyl,
  (3) halo,
  (4) $CF_3$,
  (5) —$(CH_2)_rR^9C(O)R^8$,
  (6) —$C(O)R^9$,
  (7) —$(CH_2)_tOR^8$,
  (8) —$(CH_2)_tC(O)NR^7R^8$,
  (9) $C(O)OR^8$,
  (10) —$(CH_2)_tNR^7R^8$,
  (11) $(CH_2)_rS(O)_q(CH_2)_tNR^7R^8$, and
  (12) oxido;
$R^2$ is independently selected from:
  (1) H,
  (2) unsubstituted or substituted $C_1$–$C_{10}$ alkyl,
  (3) unsubstituted or substituted aryl,
  (4) unsubstituted or substituted heterocycle,
  (5) unsubstituted or substituted $C_3$–$C_{10}$ cycloalkyl,
  (6) unsubstituted or substituted $C_2$–$C_6$ alkenyl,
  (7) unsubstituted or substituted $C_2$–$C_6$ alkynyl,
  (8) CN,
  (9) halo,
  (10) $N(R^8)_2$, and
  (11) $OR^8$;
$R^3$ is independently selected from:
  (1) H,
  (2) unsubstituted or substituted $C_1$–$C_{10}$ alkyl, and
  (3) unsubstituted or substituted aralkyl;
R7 is independently selected from:
  (1) H,
  (2) unsubstituted or substituted $C_1$–$C_6$ alkyl, and
  (3) unsubstituted or substituted aralkyl;
$R^8$ is independently selected from:
  (1) H,
  (2) unsubstituted or substituted $C_1$–$C_{10}$ alkyl, and
  (3) unsubstituted or substituted aryl;
$R^7$ and $R^8$ when attached to the same nitrogen atom, may be joined to form a 5 to 7-membered heterocycle containing, in addition to the nitrogen, one or two more heteroatoms, selected from N, O, or S, said heterocycle being optionally substituted with one to three $R^2$ substituents;
$R^9$ is independently selected from:
  (1) unsubstituted or substituted heterocycle, and
  (2) unsubstituted or substituted aryl;
V is selected from:
  (1) a bond,
  (2) aryl, and
  (3) heterocycle;
W is selected from:
  (1) aryl, and
  (2) heteroaryl, selected from pyridyl, pyrimidinyl, isoxazolyl, thiazolyl, thiadiazolyl, or pyrazinyl;

m is 0, 1, 2, or 3;
n is 0, 1, 2, 3, 4, 5, or 6;
p is 0, 1, 2, 3, or 4;
q is independently 0, 1, or 2;
t is independently 0, 1, 2, 3, 4, 5, or 6;
or a pharmaceutically acceptable salt, hydrate or stereoisomer thereof.

Another embodiment of the instant invention is illustrated by a compound of Formula II:

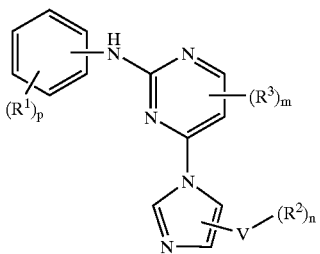

II wherein
R¹ is independently selected from:
(1) H,
(2) unsubstituted or substituted $C_1$–$C_{10}$ alkyl,
(3) halo,
(4) unsubstituted or substituted aryl,
(5) unsubstituted or substituted heterocycle,
(6) $CF_3$,
(7) —$(CH_2)_t R^9 C(O)R^8$,
(8) $C(O)R^9$, and
(9) —$(CH_2)_t OR^8$;
R² is independently selected from:
(1) H,
(2) unsubstituted or substituted $C_1$–$C_{10}$ alkyl,
(3) unsubstituted or substituted aryl,
(4) unsubstituted or substituted heterocycle,
(5) unsubstituted or substituted $C_3$–$C_{10}$ cycloalkyl,
(6) halo,
(7) $OR^8$,
(8) $N(R^8)_2$, and
(9) CN;
R³ is independently selected from:
(1) H,
(2) unsubstituted or substituted $C_1$–$C_{10}$ alkyl, and
(3) unsubstituted or substituted aralkyl;
R⁸ is independently selected from:
(1) H,
(2) unsubstituted or substituted $C_1$–$C_{10}$ alkyl, and
(3) unsubstituted or substituted aryl;
R⁹ is independently selected from unsubstituted or substituted heterocycle;
V is selected from:
(1) a bond,
(2) aryl, and
(3) heterocycle;
m is 0, 1, 2, or 3;
n is 0, 1, 2, 3, or 4;
p is 0, 1, 2, 3, or 4;
t is independently 0, 1, 2, 3, 4, 5, or 6;
or a pharmaceutically acceptable salt, hydrate or stereoisomer thereof.

Examples of compounds of the instant invention include:
4-(2-Phenyl-1H-imidazol-1-yl)-N-pyridin-4-ylpyrimidin-2-amine;
4-(2-Phenyl-1H-imidazol-1-yl)-N-pyrimidin-4-ylpyrimidin-2-amine;
4-(2-Phenyl-1H-imidazol-1-yl)-N-pyrimidin-2-ylpyrimidin-2-amine;
4-(2-Phenyl-1H-imidazol-1-yl)-N-pyrazin-2-ylpyrimidin-2-amine;
4-(2-Phenyl-1H-imidazol-1-yl)-N-(1,3,4-thiadiazol-2-yl)pyrimidin-2-amine;
N-(5-Methyl-1,3,4-thiadiazol-2-yl)-4-(2-phenyl-1H-imidazol-1-yl)pyrimidin-2-amine;
N-Isoxazol-3-yl-4-(2-phenyl-1H-imidazol-1-yl)pyrimidin-2-amine;
N-(3-Methylisoxazol-5-yl)-4-(2-phenyl-1H-imidazol-1-yl)pyrimidin-2-amine;
N-(4-Methyl-1,3-thiazol-2-yl)-4-(2-phenyl-1H-imidazol-1-yl)pyrimidin-2-amine;
N-(2-Methylpyridin-4-yl)-4-(2-phenyl-1H-imidazol-1-yl)pyrimidin-2-amine;
N-(2,6-Dimethylpyridin-4-yl)-4-(2-phenyl-1H-imidazol-1-yl)pyrimidin-2-amine;
4-(2-Phenyl-1H-imidazol-1-yl)-N-pyridin-3-ylpyrimidin-2-amine;
N-(1-Oxidopyridin-3-yl)-4-(2-phenyl-1H-imidazol-1-yl)pyrimidin-2-amine;
N-[3-Methoxy-5-(trifluoromethyl)phenyl]4-(2-phenyl-1H-imidazol-1-yl)pyrimidin-2-amine;
(3-Methyl-5-{[4-(2-phenyl-1H-imidazol-1-yl)pyrimidin-2-yl]amino}phenyl)methanol;
N-{3-[(4-Acetylpiperazin-1-yl)methyl]-5-methylphenyl}-4-(2-phenyl-1H-imidazol-1-yl)pyrimidin-2-amine;
N-(3,5-Dimethylphenyl)-4-(2-pyridin-2-yl-1H-imidazol-1-yl)pyrimidin-2-amine;
N-(3,5-Dimethylphenyl)-4-(2-pyrimidin-5-yl-1H-imidazol-1-yl)pyrimidin-2-amine;
N-(3,5-Dimethylphenyl)-4-(2-pyridin-3-yl-1H-imidazol-1-yl)pyrimidin-2-amine;
4-(2-Cyclopropyl-1H-imidazol-1-yl)-N-(3,5-dimethylphenyl)pyrimidin-2-amine;
N-(3,5-Dimethylphenyl)-4-(4-methyl-2-phenyl-1H-imidazol-1-yl)pyrimidin-2-amine;
1-{2-[(3,5-Dimethylphenyl)amino]pyrimidin-4-yl}-1H-imidazole-2-carbonitrile;
N-(3,5-Dimethylphenyl)-4-(2-methyl-1H-imidazol-1-yl)pyrimidin-2-amine;
4-(2-Amino-1H-imidazol-1-yl)-N-(3,5-dimethylphenyl)pyrimidin-2-amine;
N-(2-methylphenyl)-4-(2-phenyl-1H-imidazol-1-yl)pyrimidin-2-amine;
N-(2-methoxyphenyl)-4-(2-phenyl-1H-imidazol-1-yl)pyrimidin-2-amine;
N-(2-fluorophenyl)-4-(2-phenyl-1H-imidazol-1-yl)pyrimidin-2-amine;
N-(3-chlorophenyl)-4-(2-phenyl-1H-imidazol-1-yl)pyrimidin-2-amine;
N-(3,5-dichlorophenyl)-4-(2-phenyl-1H-imidazol-1-yl)pyrimidin-2-amine;
N-(3-fluorophenyl)-4-(2-phenyl-1H-imidazol-1-yl)pyrimidin-2-amine;
N-(3-methoxyphenyl)-4-(2-phenyl-1H-imidazol-1-yl)pyrimidin-2-amine;
N-(3-methylphenyl)-4-(2-phenyl-1H-imidazol-1-yl)pyrimidin-2-amine;
N-(3,5-dimethoxyphenyl)-4-(2-phenyl-1H-imidazol-1-yl)pyrimidin-2-amine;

N-(4-chlorophenyl)-4-(2-phenyl-1H-imidazol-1-yl)pyrimidin-2-amine;
N-(4-fluorophenyl)-4-(2-phenyl-1H-imidazol-1-yl)pyrimidin-2-amine;
N-(4-methoxyphenyl)-4-(2-phenyl-1H-imidazol-1-yl)pyrimidin-2-amine;
N-(4-methylphenyl)-4-(2-phenyl-1H-imidazol-1-yl)pyrimidin-2-amine;
N-[3,5-bis(trifluoromethyl)phenyl]-4-(2-phenyl-1H-imidazol-1-yl)pyrimidin-2-amine;
N-[3-methyl-5-(trifluoromethyl)phenyl]4-(2-phenyl-1H-imidazol-1-yl)pyrimidin-2-amine;
N-(3,5-difluorophenyl)-4-(2-phenyl-1H-imidazol-1-yl)pyrimidin-2-amine;
4-(2-phenyl-1H-imidazol-1-yl)-N-[3-(trifluoromethyl)phenyl]pyrimidin-2-amine;
N-(3,5-dimethylphenyl)-4-(2-phenyl-1H-imidazol-1-yl)pyrimidin-2-amine;
4-(2-Phenyl-1H-imidazol-1-yl)-N-pyridin-2-ylpyrimidin-2-amine;
N-{3-[(4-acetylpiperazin-1-yl)methyl]phenyl}-4-(2-phenyl-1H-imidazol-1-yl)pyrimidin-2-amine;
4-(2-Chloro-1H-imidazol-1-yl)-N-(3,5-dimethylphenyl)pyrimidin-2-amine;
N-(3,5-Dimethylphenyl)-4-[2-(3-fluorophenyl)-1H-imidazol-1-yl]pyrimidin-2-amine;

or the pharmaceutically acceptable salts thereof.

Specific examples of compounds of the instant invention include:

N-[3-methyl-5-(trifluoromethyl)phenyl]-4-(2-phenyl-1H-imidazol-1-yl)pyrimidin-2-amine;

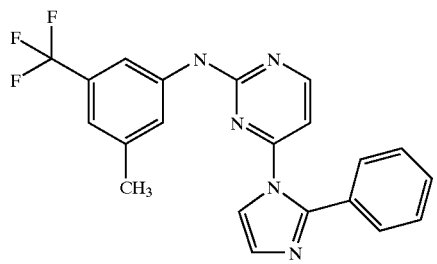

N-(3,5-dimethylphenyl)-4-(2-phenyl-1H-imidazol-1-yl)pyrimidin-2-amine;

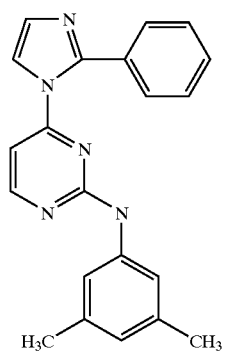

N-(3-chlorophenyl)-4-(2-phenyl-1H-imidazol-1-yl)pyrimidin-2-amine;

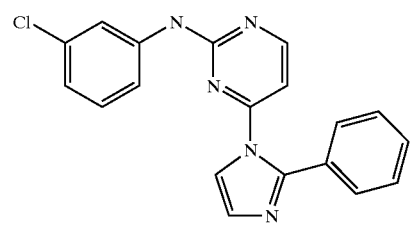

N-(3,5-dimethoxyphenyl)-2-(2-phenyl-1H-imidazol-1-yl)pyrimidin-2-amine;

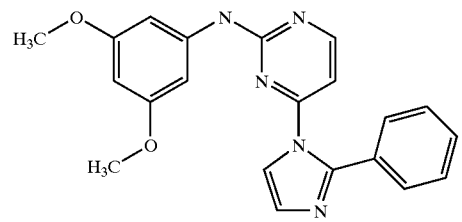

4-(2-phenyl-1H-imidazol-1-yl)-N-[3-(trifluoromethyl)phenyl]pyrimidin-2-amine;

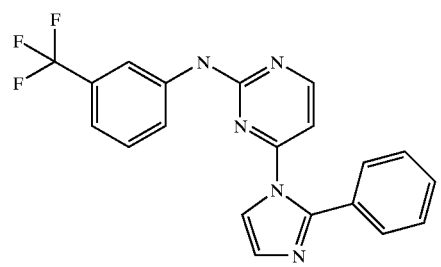

(3-methyl-5-{[4-(2phenyl-1H-imidazol-1-yl)pyrimidin-2-yl]amino}phenyl)methanol;

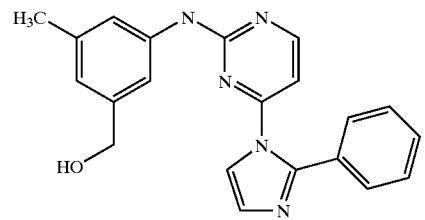

or the pharmaceutically acceptable salts thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. aryl, heterocycle, $R^1$, $R^2$ etc.) occurs more than one time in any constituent, its definition on each occurrence is independent at every other occurrence. Also, combinations of substituents and variables are permissible only if such combinations result in stable compounds.

Lines drawn into the ring systems from substituents (such as from $R^2$, $R^3$, etc.) indicate that the indicated bond may be attached to any of the substitutable ring carbon atoms or heteroatoms. If the ring system is polycyclic, it is intended that the bond be attached to any of the suitable carbon atoms or heteroatoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

As used herein, "alkyl" is intended to include both branched, straight-chain, and cyclic saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear or branched arrangement. For example, "$C_1$–$C_{10}$ alkyl" specifically includes methyl, ethyl, propyl, butyl, pentyl, hexyl, heptyl, octyl, nonyl, decyl, adamantyl, and so on.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl, tetrahydro-naphthalene, methylenecylohexyl, and the like. As used herein, examples of "$C_3$–$C_{10}$ cycloalkyl" may include, but are not limited to:

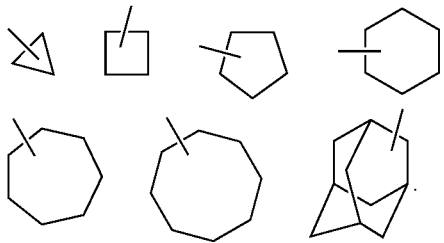

As used herein, the term "alkoxy" represents an alkyl group of indicated number of carbon atoms attached through an oxygen bridge.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to 4 non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to 3 carbon-carbon triple bonds may be present. Thus, "$C_2$–$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

As used herein, "aryl" is intended to mean any stable monocyclic, bicyclic, or tricyclic carbon ring of up to 7 atoms in each ring, wherein at least one ring is aromatic. Examples of such aryl elements include phenyl, naphthyl, tetrahydronaphthyl, indanyl, indanonyl, biphenyl, tetralinyl, tetralonyl, fluorenonyl, phenanthryl, anthryl or acenaphthyl. In cases where the aryl substituent is bicyclic and one ring is non-aromatic, it is understood that attachment is via the aromatic ring.

As appreciated by those of skill in the art, "halo" or "halogen" as used herein is intended to include chloro, fluoro, bromo and iodo.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocycle" or "heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, and the like.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively.

As used herein, "aralkyl" is intended to mean an aryl moiety, as defined above, attached through a $C_1$–$C_6$ alkyl linker, where alkyl is defined above. Examples of aralkyls include, but are not limited to, benzyl, naphthylmethyl and phenylpropyl.

As used herein, "heterocyclylalkyl" is intended to mean a heteroaryl moiety, as defined below, attached through a $C_1$–$C_6$ alkyl linker, where alkyl is defined above. Examples of heterocyclylalkyls include, but are not limited to, 2-pyridylmethyl, 2-imidazolylethyl, 2-quinolinylmethyl, 2-imidazolylmethyl and the like.

As used herein, the terms "substituted $C_1$–$C_6$ alkyl" and "substituted $C_1$–$C_6$ alkoxy" are intended to include the branch or straight-chain alkyl group of the specified number of carbon atoms, wherein the carbon atoms may be substituted with F, Cl, Br, $CF_3$, $N_3$, $NO_2$, $NH_2$, oxo, —OH, —O($C_1$–$C_6$ alkyl), $S(O)_{0-2}$, ($C_1$–$C_6$ alkyl)$S(O)_{0-2}$—, ($C_1$–$C_6$ alkyl)$S(O)_{0-2}$($C_1$–$C_6$ alkyl)-, $C_3$–$C_{10}$ cycloalkyl, $C_2$–$C_6$ alkenyl, $C_2$–$C_6$ alkynyl, —C(O)NH, ($C_1$–$C_6$ alkyl) C(O)NH—, $H_2NC(NH)$—, ($C_1$–$C_6$ alkyl)C(O)—, —O($C_1$–$C_6$ alkyl)$CF_3$, ($C_1$–$C_6$ alkyl)OC(O)—, ($C_1$–$C_6$ alkyl)O($C_1$–$C_6$ alkyl)-, ($C_1$–$C_6$ alkyl)C(O)$_2$($C_1$–$C_6$ alkyl)-, ($C_1$–$C_6$ alkyl) OC(O)NH—, aryl, benzyl, heterocycle, aralkyl, heterocyclylalkyl, halo-aryl, halo-benzyl, halo-heterocycle, cyano-aryl, cyano-benzyl and cyano-heterocycle.

As used herein, the terms "substituted aryl", "substituted heterocycle", "substituted aralkyl" and "substituted heterocyclylalkyl" are intended to include the cyclic group containing from 1 to 3 substitutents in addition to the point of attachment to the rest of the compound. Such substitutents are preferably selected from the group which includes but is not limited to F, Cl, Br, $CF_3$, $NH_2$, $N(C_1$–$C_6$ alkyl)$_2$, $NO_2$, CN, $N_3$, $C_1$–$C_{20}$ alkyl, $C_1$–$C_6$ alkoxy, —OH, —O($C_1$–$C_6$ alkyl), $S(O)_{0-2}$, ($C_1$–$C_6$alkyl)$S(O)_{0-2}$—, ($C_1$–$C_6$ alkyl)$S(O)_{0-2}$($C_1$–$C_6$ alkyl)-, ($C_1$–$C_6$ alkyl)C(O)NH—, $H_2N$—C(NH)—, ($C_1$–$C_6$ alkyl)C(O)—, ($C_1$–$C_6$ alkyl)OC(O)—, ($C_1$–$C_6$ alkyl)O($C_1$–$C_6$ alkyl)-, ($C_1$–$C_6$ alkyl)C(O)$_2$($C_1$–$C_6$ alkyl)-, ($C_1$–$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The moiety formed when, in the definition of $R^7$ and $R^8$ are joined to form a ring, is illustrated by, but not limited to, the following:

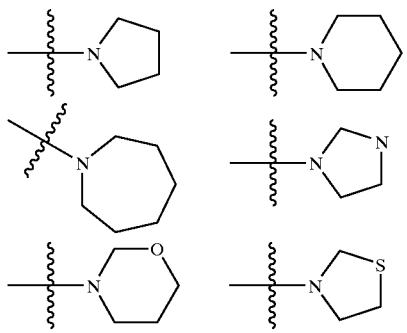

Preferably, $R^2$ is independently selected from H, unsubstituted or substituted $C_1$–$C_{10}$ alkyl, halo, $N(R^8)_2$, CN, and unsubstituted or substituted $C_3$–$C_{10}$ cycloalkyl.

Preferably, $R^3$ is independently selected from H, unsubstituted or substituted $C_1$–$C_{10}$ alkyl, and unsubstituted or substituted aryl. Most preferred, $R^3$ is independently selected from H.

Preferably, when V is a bond, $R^2$ is not an aryl or heterocycle.

Preferably, W is selected from phenyl, pyridyl, pyrimidinyl, pyrazinyl, thiazolyl, thiadiazolyl, and isoxazolyl.

Preferably, n and p are independently selected from 0, 1, 2 or 3.

Preferably, t is independently selected from 0, 1, 2, 3 or 4. More preferably, t is independently selected from 0, 1 or 2.

It is intended that the definition of any substituent or variable (e.g., $R^2$, $R^3$, n, etc.) at a particular location in a molecule be independent of its definitions elsewhere in that molecule. Thus, —$N(R^4)_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions as shown in the following schemes, in addition to other standard manipulations that are known in the literature or exemplified in the experimental procedures. These schemes, therefore, are not limited by the compounds listed nor by any particular substituents employed for illustrative purposes. Substituent numbering as shown in the schemes do not necessarily correlate to that used in the claims.

SCHEME A

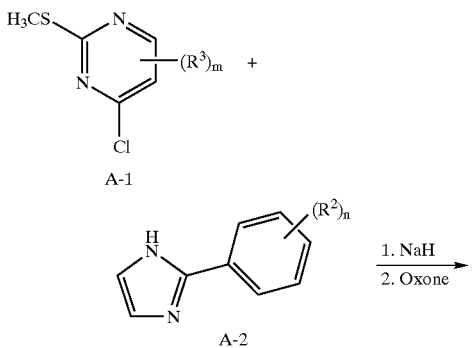

-continued

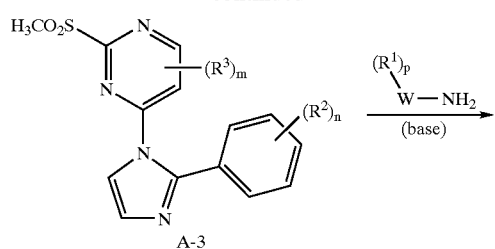

A-3

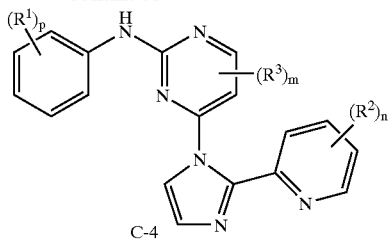

C-4

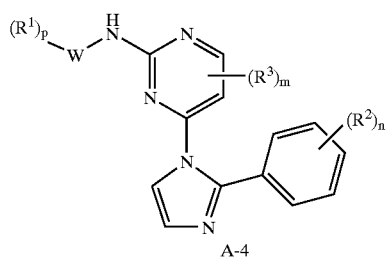

A-4

SCHEME B

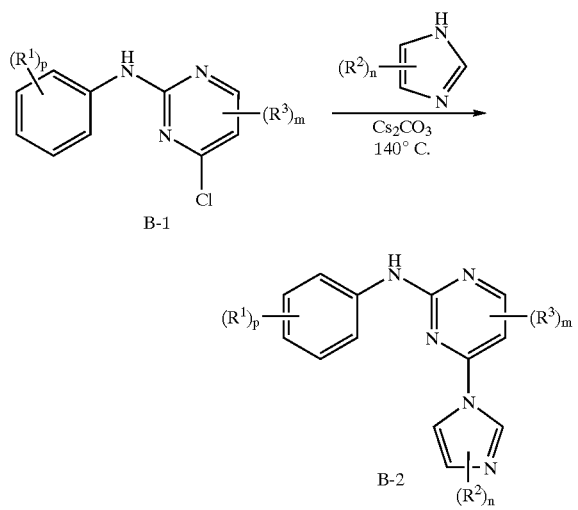

SCHEME C

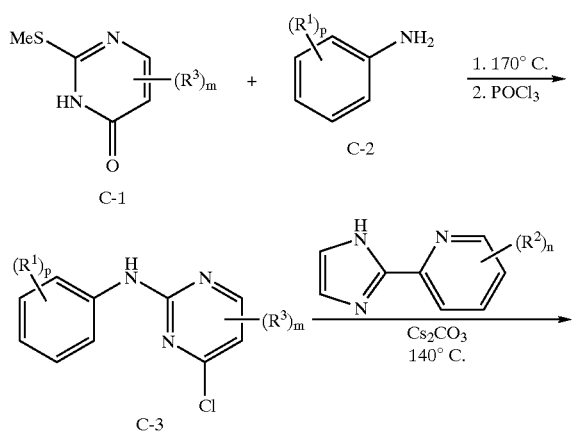

Utility

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like).

Included within the scope of the present invention is a pharmaceutical composition which is comprised of a compound of Formula I as described above and a pharmaceutically acceptable carrier. The present invention also encompasses a method of treating or preventing cancer in a mammal in need of such treatment which is comprised of administering to said mammal a therapeutically effective amount of a compound of Formula I. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, gioblastomas and breast carcinoma.

Also included is a method of treating or preventing a disease in which angiogenesis is implicated, which is comprised of administering to a mammal in need of such treatment a therapeutically effective amount of a compound of Formula I. Such a disease in which angiogenesis is implicated is ocular diseases such as retinal vascularization, diabetic retinopathy, age-related macular degeneration, and the like.

Also included is a method of inhibiting at least two tyrosine kinase receptors, selected from KDR, EGFR or SRC, by administering a therapeutically effective amount of a compound of Formula I.

Also included within the scope of the present invention is a method of treating or preventing inflammatory diseases which comprises administering to a mammal in need of such treatment a therapeutically effective amount of a compound of Formula I. Examples of such inflammatory diseases are rheumatoid arthritis, psoriasis, contact dermatitis, delayed hypersensitivity reactions, and the like.

Also included is a method of treating or preventing a tyrosine kinase-dependent disease or condition in a mammal which comprises administering to a mammalian patient in need of such treatment a therapeutically effective amount of a compound of Formula I. The therapeutic amount varies according to the specific disease and is discernable to the skilled artisan without undue experimentation.

A method of treating or preventing retinal vascularization which is comprised of administering to a mammal in need of such treatment a therapeutically effective amount of compound of Formula I is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

The invention also contemplates the use of the instantly claimed compounds in combination with a second compound selected from the group consisting of:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

The preferred second angiogenesis inhibitor is selected from the group consisting of a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a compound of Formula I in combination with radiation therapy and/or in combination with a compound selected from the group consisting of:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formula I in combination with paclitaxel or trastuzumab.

These and other aspects of the invention will be apparent from the teachings contained herein.

The instant compounds are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, and the like) and inflammation (psoriasis, rheumatoid arthritis, and the like).

The compounds of the instant invention may be administered to patients for use in the treatment of cancer. The instant compounds inhibit tumor angiogenesis, thereby affecting the growth of tumors (J. Rak et al. *Cancer Research*, 55:4575–4580, 1995). The anti-angiogenesis properties of the instant compounds are also useful in the treatment of certain forms of blindness related to retinal vascularization.

It has been shown that simultaneously targeting multiple angiogenic factors may improve survival of mammals with cancer metastases. (R. M. Shaheen et al., *Cancer Research*, 61:1464–1468, 2001). The disclosed compounds are also useful in a method of treating cancer by administering a therapeutically effective amount of a compound of Formula I in order to inhibit at least two tyrosine kinase receptors, particularly KDR, EGFR and SRC.

The instant compounds can also be used to prevent or treat tissue damage during bacterial meningitis, such as tuberculous meningitis. (Matsuyama et al., *J. Neurol. Sci.* 186:75–79 (2001)). The instant invention therefore encompasses a method of treating or preventing tissue damage due to bacterial meningitis which comprises administering a therapeutically effective amount of a compound of Formula 1. Studies have shown that VEGF is secreted by inflammatory cells during bacterial meningitis and that VEGF contributes to blood-brain barrier disruption. (van der Flier et al., *J. Infectious Diseases*, 183:149–153 (2001)). The claimed compounds can inhibit VEGF-induced vascular permeability and therefore serve to prevent or treat blood-brain barrier disruption associated with bacterial meningitis.

The disclosed compounds are also useful in the treatment of certain bone-related pathologies, such as osteosarcoma, osteoarthritis, and rickets, also known as oncogenic osteomalacia. (Hasegawa et al., Skeletal Radiol., 28, pp.41–45, 1999; Gerber et al., Nature Medicine, Vol. 5, No. 6, pp.623–628, June 1999). And since VEGF directly promotes osteoclastic bone resorption through KDR/Flk-1 expressed in mature osteoclasts (FEBS Let. 473:161–164 (2000); Endocrinology, 141:1667 (2000)), the instant compounds are also useful to treat and prevent conditions related to bone resorption, such as osteoporosis and Paget's disease.

The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999); *Nature Med* 7:222–227 (2001)).

The instant compounds are useful in the treatment of preeclampsia. Studies have shown that the action of VEGF on the Flt-1 receptor is pivotal in the pathogenesis of preeclampsia. (*Laboratory Investigation* 79:1101–1111 (September 1999)). Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed compounds serve to treat preeclampsia via their action on the tyrosine kinase domain of the Flt-1 receptor.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, in the case of bone-related disorders, combinations that would be useful include those with antiresorptive bisphosphonates, such as alendronate and risedronate; integrin blockers (defined further below), such as $\alpha_v\beta_3$ antagonists; conjugated estrogens used in hormone replacement therapy, such as PREMPRO®, PREMARIN® and ENDOMETRION®; selective estrogen receptor modulators (SERMs), such as raloxifene, droloxifene, CP-336,156 (Pfizer) and lasofoxifene; cathespin K inhibitors; and ATP proton pump inhibitors.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art (see WO 00/61186).

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl] acridine-2-(6H)propanamine, 1-amino-9-ethyl-5-fluoro-2,3-dihydro-9-hydroxy-4-methyl-1H, 12H-benzo[de]pyrano[3',4':b,7]indolizino[1,2b]quinoline-10,13(9H,15H)dione, lurtotecan, 7-[2-(N-isopropylamino)ethyl]-(20S) camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido [4,3-b]carbazole-1-carboxamide, asulacrine, (5a, 5aB, 8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

"Antiproliferative agents" includes antisense RNA and DNA oligonucleotides such as G3139, ODN698, RVASKRAS, GEM231, and NX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulae of these and additional HMG-CoA reductase inhibitors that may be used in the instant methods are described at page 87 of M. Yalpani, "Cholesterol Lowering Drugs", Chemistry & Industry, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

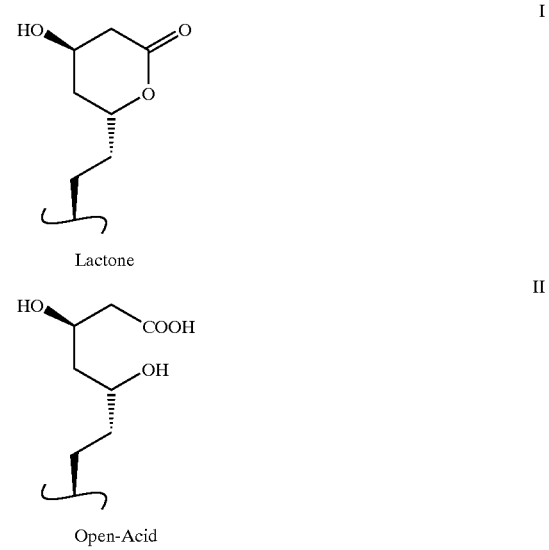

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethyl amine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2 (1H)-quinolinone, (−)-6-[amino(4-chlorophenyl)(1-methyl-1H-imidazol-5-yl)methyl]-4-(3-chlorophenyl)-1-methyl-2 (1H)-quinolinone, (+)-6-[amino(4-chlorophenyl)(1-methyl-1H-imidazol-5-yl)methyl]-4-(3-chlorophenyl)-1-methyl-2 (1H)-quinolinone, 5 (S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H, 17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H, 17H-18,21-ethano-6, 10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo [d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp.1394–1401 (1999).

Examples of HIV protease inhibitors include amprenavir, abacavir, CGP-73547, CGP-61755, DMP450, indinavir, nelfinavir, tipranavir, ritonavir, saquinavir, ABT-378, AG 1776, and BMS-232,632. Examples of reverse transcriptase inhibitors include delaviridine, efavirenz, GS-840, HBY097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF. (see, Nature Biotechnology, Vol. 17, pp.963–968 (October 1999); Kim et al., Nature, 362, 841–844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 μM or less as measured by the cell or microsomal assay disclosed herein.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or microsomal assay disclosed hereinunder. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Other examples of specific inhibitors of COX-2 include the following:

3-(3-fluorophenyl)-4-(4-(methylsulfonyl)phenyl)-2-(5H)-furanone;

3-(3,4-difluorophenyl)-4-(4-(methylsulfonyl)phenyl)-2-(5H)-furanone;

3-(3,4-dichlorophenyl)-4-(4-(methylsulfonyl)phenyl)-2-(5H)-furanone;
3-phenyl-4-(4-(methylsulfonyl)phenyl)-2-(5H)-furanone;
5,5-dimethyl-3-(3-fluorophenyl)-4-(methylsulfonyl)phenyl)-2-(5H)-furanone;
3-(4-methylsulfonyl)phenyl-2-phenyl-5-trifluoromethylpyridine;
2-(3-chlorophenyl)-3-(4-methylsulfonyl)phenyl-5-trifluoromethyl-pyridine;
2-(4-chlorophenyl)-3-(4-methylsulfonyl)phenyl-5-trifluoromethyl-pyridine;
2-(4-fluorophenyl)-3-(4-methylsulfonyl)phenyl-5-trifluoromethyl-pyridine;
3-(4-methylsulfonyl)phenyl-2-(3-pyridinyl)-5-trifluoromethylpyridine;
5-methyl-3-(4-methylsulfonyl)phenyl-2-phenylpyridine;
2-(4-chlorophenyl)-5-methyl-3-(4-methylsulfonyl)phenylpyridine;
5-methyl-3-(4-methylsulfonyl)phenyl-2-(3-pyridinyl)pyridine;
5-chloro-2-(4-chlorophenyl)-3-(4-methylsulfonyl)phenylpyridine;
5-chloro-3-(4-methylsulfonyl)phenyl-2-(2-pyridinyl)pyridine;
5-chloro-3-(4-methylsulfonyl)phenyl-2-(3-pyridinyl)pyridine;
5-chloro-3-(4-methylsulfonyl)phenyl-2-(4-pyridinyl)pyridine;
5-chloro-3-(4-methylsulfonyl)phenyl-2-(2-methyl-5-pyridinyl)pyridine;
2-(4-chlorophenyl)-3-(4-methylsulfonyl)phenylpyridinyl-5-carboxylic acid methyl ester;
2-(4-chlorophenyl)-3-(4-methylsulfonyl)phenylpyridinyl-5-carboxylic acid;
5-cyano-2-(4-chlorophenyl)-3-(4-methylsulfonyl)phenylpyridine;
5-chloro-3-(4-methylsulfonyl)phenyl-2-(3-pyridyl)pyridine hydromethanesulfonate;
5-chloro-3-(4-methylsulfonyl)phenyl-2-(3-pyridyl)pyridine hydrochloride;
5-chloro-3-(4-methylsulfonyl)phenyl-2-(2-methyl-5-pyridinyl)pyridine hydrochloride;
5-chloro-3-(4-methylsulfonyl)phenyl-2-(2-ethyl-5-pyridinyl)pyridine;
5-chloro-3-(4-methylsulfonyl)phenyl-2-(2-ethyl-5-pyridinyl)pyridine hydromethanesulfonate;
3-(3,4-difluorophenoxy)-5,5-dimethyl-4-(4-(methylsulfonyl)phenyl)-5H-furan-2-one;
3-(3-fluorophenoxy)-5,5-dimethyl-4-(4-(methylsulfonyl)phenyl)-5H-furan-2-one;
3-(3,5-difluorophenoxy)-5,5-dimethyl-4-(methylsulfonyl)phenyl)-5H-furan-2-one;
3-phenoxy-5,5-dimethyl-4-(4-(methylsulfonyl)phenyl)-5H-furan-2-one;
3-(2,4-difluorophenoxy)-5,5-dimethyl-4-(4-(methylsulfonyl)phenyl)-5H-furan-2-one;
3-(4-chlorophenoxy)-5,5-dimethyl-4-(4-(methylsulfonyl)phenyl)-5H-furan-2-one;
3-(3,4-dichlorophenoxy)-5,5-dimethyl-4-(methylsulfonyl)phenyl)-5H-furan-2-one;
3-(4-fluorophenoxy)-5,5-dimethyl-4-(4-(methylsulfonyl)phenyl)-5H-furan-2-one;
3-(4-fluorophenylthio)-5,5-dimethyl-4-(4-(methylsulfonyl)phenyl)-5H-furan-2-one;
3-(3,5-difluorophenylthio)-5,5-dimethyl-4-(4-(methylsulfonyl)phenyl)-5H-furan-2-one;
3-phenylthio-5,5-dimethyl-4-(4-(methylsulfonyl)phenyl)-5H-furan-2-one;
3-(N-phenylamino)-5,5-dimethyl-4-(4-(methylsulfonyl)phenyl)-5H-furan-2-one;
3-(N-methyl-N-phenylamino)-5,5-dimethyl-4-(4-(methylsulfonyl)phenyl)-5H-furan-2-one;
3-cyclohexyloxy-5,5-dimethyl-4-(4-(methylsulfonyl)phenyl)-5H-furan-2-one;
3-phenylthio-4-(4-(methylsulfonyl)phenyl)-5H-furan-2-one;
3-benzyl-5,5-dimethyl-4-(4-(methylsulfonyl)phenyl)-5H-furan-2-one;
3-(3,4-difluorophenylhydroxymethyl)-5,5-dimethyl-4-(4-(methylsulfonyl)phenyl)-5H-furan-2-one;
3-(3,4-difluorobenzoyl)-5,5-dimethyl-4-(4-(methylsulfonyl)phenyl)-5H-furan-2-one;
3-benzoyl-5,5-dimethyl-4-(4-(methylsulfonyl)phenyl)-5H-furan-2-one;
4-(4-(methylsulfonyl)phenyl)-3-phenoxy-1-oxaspiro[4,4]non-3-en-2-one;
4-(4-(methylsulfonyl)phenyl)-3-phenylthio-1-oxaspiro[4,4]non-3-en-2-one;
4-(2-oxo-3-phenylthio-1-oxa-spiro[4,4]non-3-en-4-yl)benzenesulfonamide;
3-(4-fluorobenzyl)-5,5-dimethyl-4-(4-(methylsulfonyl)phenyl)-5H-furan-2-one;
3-(3,4-difluorophenoxy)-5-methoxy-5-methyl-4-(4-(methylsulfonyl)phenyl)-5H-furan-2-one;
3-(5-chloro-2-pyridyloxy)-5,5-dimethyl-4-(4-(methylsulfonyl)phenyl)-5H-furan-2-one;
3-(2-pyridyloxy)-5,5-dimethyl-4-(4-(methylsulfonyl)phenyl)-5H-furan-2-one;
3-(6-methyl-2-pyridyloxy)-5,5-dimethyl-4-(4-(methylsulfonyl)phenyl)-5H-furan-2-one;
3-(3-isoquinolinoxy)-5,5-dimethyl-4-(4-(methylsulfonyl)phenyl)-5H-furan-2-one;
3-(4-(methylsulfonyl)phenyl)-2-phenoxycyclopent-2-enone;
3-(4-(methylsulfonyl)phenyl)-2-(3,4-difluorophenoxy)cyclopent-2-enone;
5,5-dimethyl-4-(4-methylsulfonylphenyl)-3-(5-bromopyridin-2-yloxy)-5H-furan-2-one;
5,5-dimethyl-4-(4-methylsulfonylphenyl)-3-(2-propoxy)-5H-furan-2-one;
2-(3,4-difluorophenoxy)-3-(4-methylsulfonylphenyl)-cyclopent-2-enone;
3-(5-benzothiophenyloxy)-5,5-dimethyl-4-(4-(methylsulfonyl)phenyl)-5H-furan-2-one;
5,5-dimethyl-4-(4-methylsulfonyl-phenyl)-3-(pyridyl-4-oxy)-5H-furan-2-one;
5,5-dimethyl-4-(4-methylsulfonylphenyl)-3-(pyridyl-3-oxy)-5H-furan-2-one;
3-(2-methyl-5-pyridyloxy)-5,5-dimethyl-4-(4-(methylsulfonyl)phenyl)-5H-furan-2-one;
3-(2-fluoro-4-trifluoromethyl)phenoxy-4-(4-methylsulfonyl)phenyl)-5,5-dimethyl-5H-furan-2-one;
3-(5-chloro-2-pyridylthio)-5,5-dimethyl-4-(4-methylsulfonyl)phenyl-5H-furan-2-one;
2-(3,5-difluorophenoxy)-3-(4-methylsulfonylphenyl)-cyclopent-2-enone;
3-(2-pyrimidinoxy)-5,5-dimethyl-4-(4-methylsulfonyl)phenyl-5H-furan-2-one;
3-(3-methyl-2-pyridyloxy)-5,5-dimethyl-4-(4-methylsulfonyl)phenyl-5H-furan-2-one;
3-(3-chloro-5-pyridyloxy)-5,5-dimethyl-4-(4-(methylsulfonyl)phenyl)-5H-furan-2-one;
3-(3-(1,2,5-thiadiazolyl)oxy)-4-(4-(methylsulfonyl)phenyl)-5,5-dimethyl-5H-furan-2-one;
3-(5-isoquinolinoxy)-5,5-dimethyl-4-(4-methylsulfonyl)phenyl-5H-furan-2-one;

3-(6-amino-2-pyridyloxy)-5,5-dimethyl-4-(4-(methylsulfonyl)phenyl)-5H-furan-2-one;
3-(3-chloro-4-fluoro)phenoxy-4-(methylsulfonyl)phenyl)-5,5-dimethyl-5H-furan-2-one;
3-(6-quinolinoxy)-5,5-dimethyl-4-(4-(methylsulfonyl)phenyl)-5H-furan-2-one;
3-(5-nitro-2-pyridyloxy)-5,5-dimethyl-4-(4-methylsulfonyl)phenyl-5H-furan-2-one;
3-(2-thiazolylthio)-5,5-dimethyl-4-(4-(methylsulfonyl)phenyl)-5H-furan-2-one;
3-(3-chloro-5-pyridyloxy)-5,5-dimethyl-4-(4-(methylsulfonyl)phenyl)-5H-furan-2-one;
5,5-dimethyl-4-(4-methylsulfonylphenyl)-3-(2-propoxy)-5H-furan-2-one;
3-(3-trifluoromethyl)phenoxy-4-(4-methylsulfonyl)phenyl)-5,5-dimethyl-5H-furan-2-one;
5,5-dimethyl-(4-(4-methylsulfonyl)phenyl)-3-(piperidine-1-carbonyl)-5-H-furan-2-one;
5,5-dimethyl-3-(2-Butoxy)-4-(4-methylsulfonylphenyl)-5H-furan-2-one;
5,5-dimethyl-4-(4-methylsulfonylphenyl)-3-(3-pentoxy)-5H-furan-2-one;
2-(5-chloro-2-pyridyloxy)-3-(4-methylsulfonyl)phenylcyclopent-2-enone;
3-(4-methyl-2-pyridyloxy)-5,5-dimethyl-4-(4-methylsulfonyl)phenyl-5H-furan-2-one;
(5R)-3-(3,4-difluorophenoxy)-5-ethyl-5-methyl-4-(4-methylsulfonyl)phenyl-5H-furan-2-one;
(5R)-3-(4-chlorophenoxy)-5-ethyl-5-methyl-4-(4-methylsulfonyl)phenyl-5H-furan-2-one;
3-(2-methyl-3-pyridyloxy)-5,5-dimethyl-4-(4-methylsulfonyl)phenyl-5H-furan-2-one;
3-(4-methyl-5-nitro-2-pyridyloxy)-5,5-dimethyl-4-(4-methylsulfonyl)phenyl-5H-furan-2-one;
3-(5-chloro-4-methyl-2-pyridyloxy)-5,5-dimethyl-4-(4-methylsulfonyl)phenyl-5H-furan-2-one;
3-(5-fluoro-4-methyl-2-pyridyloxy)-5,5-dimethyl-4-(4-methylsulfonyl)phenyl-5H-furan-2-one;
3-(3-chloro-2-pyridyloxy)-5,5-dimethyl-4-(4-methylsulfonyl)phenyl-5H-furan-2-one;
3-(4-fluorophenoxy)-5-methyl-4-(4-methylsulfonyl)phenyl-5-propyl-5H-furan-2-one;
3-(N,N-diethylamino)-5,5-dimethyl-4-(4-(methylsulfonyl)phenyl)-5H-furan-2-one;
5,5-dimethyl-4-(4-methylsulfonyl-phenyl)-3-(3,5-dichloro-2-pyridyloxy)-5H-furan-2-one;
(5R)-3-(4-bromophenoxy)-5-ethyl-5-methyl-4-(4-methylsulfonyl)phenyl-5H-furan-2-one;
(5R)-3-(4-methoxyphenoxy)-5-ethyl-5-methyl-4-(4-methylsulfonyl)phenyl-5H-furan-2-one;
(5R)-3-(5-chloro-2-pyridyloxy)-5-methyl-4-(4-methylsulfonyl)phenyl-5-(2,2,2-trifluoroethyl)-5H-furan-2-one;
3-(5-chloro-2-pyridyloxy)-5-methyl-4-(4-methylsulfonyl)phenyl-5-propyl-5H-furan-2-one;
3-(1-cyclopropyl-ethoxy)-5,5-dimethyl-4-(4-methyl sulfonyl)phenyl)-5H-furan-2-one;
5-methyl-4-(4-(methylsulfonyl)phenyl)-3-(2-(propoxy)-5-(2-trifluoroethyl)-5H-furan-2-one;
5(R)-5-ethyl-5-methyl-4-(4-(methylsulfonyl)phenyl)-3-(2-propoxy)-5H-furan-2-one;
5,5-dimethyl-3-(2,2-dimethylpropyloxy)-4-(4-(methylsulfonyl)phenyl)-5H-furan-2-one;
5(R)-3-(1-cyclopropyl-ethoxy)-5-ethyl-5-methyl-4-(4-(methyl sulfonyl)phenyl)-5H-furan-2-one;
5(S)-5-ethyl-5-methyl-4-(4-(methylsulfonyl)phenyl)-3-(2-propoxy)-5H-furan-2-one;
3-(1-cyclopropylethoxy)-5,5-dimethyl-4-(4-(methylsulfonyl)phenyl)-5H-furan-2-one;
3-(1-cyclopropylethoxy)-5,5-dimethyl-4-(4-(methylsulfonyl)phenyl)-5H-furan-2-one;
5,5-dimethyl-3-(isobutoxy)-4-(4-(methylsulfonyl)phenyl)-5H-furan-2-one;
3-(4-bromophenoxy)-5,5-dimethyl-4-(4-(methylsulfonyl)phenyl)-5H-furan-2-one;
3-(2-quinolinoxy)-5,5-dimethyl-4-(4-(methylsulfonyl)phenyl)-5H-furan-2-one;
3-(2-chloro-5-pyridyloxy)-5,5-dimethyl-4-(4-(methylsulfonyl)phenyl)-5H-furan-2-one;
3-(6-benzothiazolyloxy)-5,5-dimethyl-4-(4-(methylsulfonyl)phenyl)-5H-furan-2-one;
3-(6-chloro-2-pyridyloxy)-5,5-dimethyl-4-(4-(methylsulfonyl)phenyl)-5H-furan-2-one;
3-(4-quinazolyloxy)-5,5-dimethyl-4-(4-(methylsulfonyl)phenyl)-5H-furan-2-one;
(5R)-3-(5-fluoro-2-pyridyloxy)-5-ethyl-5-methyl-4-(4-methylsulfonyl)phenyl-5H-furan-2-one;
(5R)-3-(4-fluorophenoxy)-5-ethyl-5-methyl-4-(4-methylsulfonyl)phenyl-5H-furan-2-one;
(5R)-3-(5-fluoro-2-pyridyloxy)-5-methyl-4-(4-methylsulfonyl)phenyl-5-(2,2,2-trifluoroethyl)-5H-furan-2-one;
3-(1'-isoquinolinyloxy)-5,5-dimethyl-4-(methylsulfonyl)phenyl-5H-furan-2-one;
(5R)-3-(4-fluorophenoxy)-5-methyl-4-(4-methylsulfonyl)phenyl-5-(2,2,2-trifluoroethyl)-5H-furan-2-one;
3-(3-fluoro-2-pyridyloxy)-5,5-dimethyl-4-(4-methylsulfonyl)phenyl-5H-furan-2-one;
(5R)-3-(3,4-difluorophenoxy)-5-methyl-4-(4-methylsulfonyl)phenyl-5-(2,2,2-trifluoroethyl)-5H-furan-2-one;
(5R)-3-(5-chloro-2-pyridyloxy)-5-ethyl-5-methyl-4-(4-methylsulfonyl)phenyl-5H-furan-2-one;
3-(3,4-difluorophenoxy)-5-methyl-5-tri fluoromethyl-4-(4-methylsulfonyl)phenyl-5H-furan-2-one;
3-(3,4-difluorophenoxy)-5-methyl-4-(4-(methylsulfonyl)phenyl)-5-propyl-5H-furan-2-one;
3-cyclobutyloxy-5,5-dimethyl-4-(4-methylsulfonylphenyl-5H-furan-2-one;
3-(1-indanyloxy)-5,5-dimethyl-4-(4-(methylsulfonyl)phenyl)-5H-furan-2-one;
3-(2-indanyloxy)-5,5-dimethyl-4-(4-(methylsulfonyl)phenyl)-5H-furan-2-one;
3-cyclopentyloxy-5,5-dimethyl-4-(4-methylsulfonylphenyl)5H-furan-2-one;
3-(3,3-dimethylcyclopentyloxy)-5,5-dimethyl-4-(4-methylsulfonyl-phenyl)-5H-furan-2-one;
3-isopropoxy-5-methyl-4-(4-methylsulfonylphenyl)-5-propyl-5H-furan-2-one;
3-(2-methoxy-5-pyridyloxy)-5,5-dimethyl-4-(4-methylsulfonyl)phenyl-5H-furan-2-one;
3-(5-methyl-2-pyridyloxy)-5,5-dimethyl-4-(4-methylsulfonyl)phenyl-5H-furan-2-one;
(5RS)-3-(3,4-difluorophenoxy)-5-methyl-4-(4-methylsulfonyl)phenyl-5-(2,2,2-trifluoroethyl)-5H-furan-2-one;
3-(3-chloro-4-methoxyphenoxy)-5,5-dimethyl-4-(4-methylsulfonyl)phenyl-5H-furan-2-one;
(5R)-3-(3-chloro-4-methoxyphenoxy)-5-ethyl-5-methyl-4-(4-methylsulfonyl)phenyl-5H-furan-2-one;
(5R)-3-(4-chlorophenoxy)-5-trifluoroethyl-5-methyl-4-(4-methylsulfonyl)phenyl-5H-furan-2-one;
(5R)-3-(4-bromophenoxy)-5-trifluoroethyl-5-methyl-4-(4-methylsulfonyl)phenyl-5H-furan-2-one;

5-cyclopropylmethyl-3-(3,4-difluorophenoxy)-5-methyl-(4-methylsulfonyl)phenyl-5H-furan-2-one;
(5R)-3-(3-fluorophenoxy)-5-ethyl-5-methyl-4-(4-methylsulfonyl)phenyl-5H-furan-2-one;
(5R)-3-(4-chloro-3-fluorophenoxy)-5-ethyl-5-methyl-4-(4-methylsulfonyl)phenyl-5H-furan-2-one;
(5R)-3-phenoxy-5-ethyl-5-methyl-4-(4-methylsulfonyl)phenyl-5H-furan-2-one;
(5R)-3-(4-chloro-3-methylphenoxy)-5-ethyl-5-methyl-4-(4-methylsulfonyl)phenyl-5H-furan-2-one;
3-(4-chloro-3-methylphenoxy)-5-5-dimethyl-4-(4-methylsulfonyl)phenyl-5H-furan-2-one;
(5R)-3-(5-bromo-2-pyridyloxy)-4-(4-methylsulfonylphenyl)-5-methyl-5-(2,2,2-trifluoroethyl)-5H-furan-2-one;
(5R)-3-(5-bromo-2-pyridyloxy)-4-(4-methylsulfonylphenyl)-5-ethyl-5-methyl-5H-furan-2-one;
3-(5-chloro-6-methyl-2-pyridyloxy)-5,5-dimethyl-4-(4-methylsulfonyl)phenyl-5H-furan-2-one;
3-(5-cyclopropyl-2-pyridyloxy)-5,5-dimethyl-4-(4-methylsulfonyl)phenyl-5H-furan-2-one;
3-(1-cyclopropylethoxy)-4-(4-methylsulfonyl)phenyl-5H-furan-2-one; and
3-(cyclopropylmethoxy)-4-(4-methylsulfonyl)phenyl-5H-furan-2-one;
or a pharmaceutically acceptable salt or stereoisomer thereof.

Inhibitors of COX-2 that are particularly useful in the instant method of treatment are:
3-phenyl-4-(4-(methylsulfonyl)phenyl)-2-(5H)-furanone; and

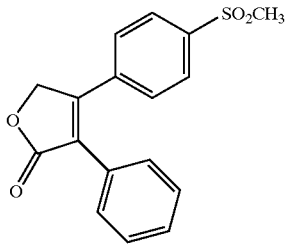

5-chloro-3-(4-methylsulfonyl)phenyl-2-(2-methyl-5-pyridinyl)pyridine;

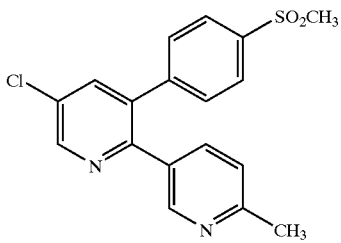

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha v\beta_6$, $\alpha v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha v\beta_3$, $\alpha v\beta_5$, $\alpha v\beta_6$, $\alpha v\beta_8$, $\alpha_1\beta_1$, $\alpha_2\beta_1$, $\alpha_5\beta_1$, $\alpha_6\beta_1$ and $\alpha_6\beta_4$ in Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

EXAMPLES

Examples provided are intended to assist in a further understanding of the invention. Particular materials employed, species and conditions are intended to be further illustrative of the invention and not limiting of the reasonable scope thereof.

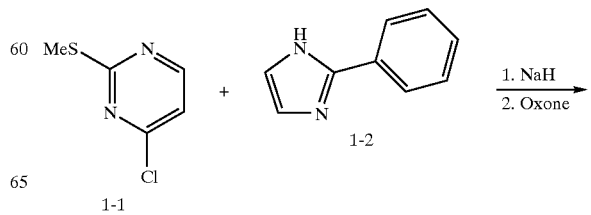

SCHEME 1

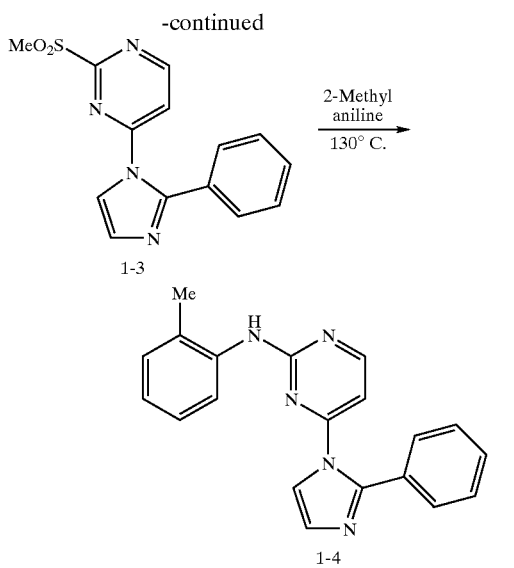

2-(Methylsulfonyl)-4-(2-phenyl-1H-imidazol-1-yl)pyrimidine (1-3)

2-Phenylimidazole (1-2, 50 g, 347 mmol) was dissolved in 400 ml DMF and the resulting solution was cooled to 0° C. Sodium hydride (8.32 g of solid NaH, plus 13.9 g of a 60% dispersion in mineral oil, 347 mmol) was added and the mixture was stirred for 10 minutes. 4-Chloro-2-(methylthio)pyrimidine (1-1, 55.7 g, 347 mmol) was then added over 2 minutes. The reaction was then heated to 100° C. After stirring overnight the reaction was partitioned between water and EtOAc. The organic phase was washed 2× with water, dried over $Na_2SO_4$, filtered and concentrated. Purification by flash column chromatography (eluting with 50:50 to 70:30 EtOAc/Hexane) afforded 2-(methylthio)-4-(2-phenyl-1H-imidazol-1-yl)pyrimidine.

To a solution of 2-(methylthio)-4-(2-phenyl-1H-imidazol-1-yl)pyrimidine (2.0 g, 7.45 mmol) in EtOAc (25 mL) was added sodium tungstate dihydrate (110 mg, 0.37 mmol) then 5.1 mL 30% $H_2O_2$ at room temperature. After 18 hours the mixture was diluted with $H_2O$ and the layers separated. The aqueous was extracted with EtOAc (2×). The combined organic layers were dried ($MgSO_4$), filtered, and concentrated. The residue was crystallized from EtOAc/hexanes to give the title compound as a pale yellow solid. $^1$H-NMR (300 MHz, $d_6$-DMSO) δ 9.15 (d, J=5.37 Hz, 1H), 8.02 (s, 1H), 7.77 (d, J=5.37 Hz, 1H), 7.45 (m, 5H), 7.35 (s, 1H), 3.00 (s, 3H).

General Procedure for the Preparation of N-aryl-4-(2-phenyl-1H-imidazol-1-yl)pyrimidin-2-amines 2-(Methylsulfonyl)-4-(2-phenyl-1H-imidazol-1-yl)pyrimidine (1-3, 0.17 mmol) and the appropriate aniline (0.83 mmol) were combined neat and heated to 130° C. for about 2.5 to about 24 hours. The reaction was allowed to cool to room temperature and was directly purified by reverse phase chromatography (gradient, 5–100% $CH_3CN$/$H_2O$+0.1% TFA). The fractions containing the desired compound were concentrated to dryness to afford the TFA salt.

N-(2-methylphenyl)-4-(2-phenyl-1H-imidazol-1-yl)pyrimidin-2-amine (1-4)

Prepared by the general procedure by heating for 2.5 hours to afford the desired compound as a light yellow oil. TFA salt: $^1$H NMR ($CD_3OD$) δ 8.48 (d, 1H, J=5.12 Hz), 8.04 (d, 1H, J=1.83 Hz), 7.77 (d, 1H, J=2.02 Hz), 7.67 (m, 1H), 7.56 (m, 4H), 7.19 (m, 1H), 7.06 (m, 3H), 6.69 (d, 1H, J=5.13 Hz), 2.20 (s, 3H). [M+H]+=328.1.

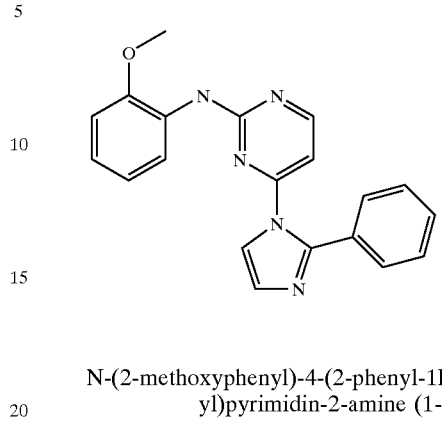

N-(2-methoxyphenyl)-4-(2-phenyl-1H-imidazol-1-yl)pyrimidin-2-amine (1-5)

Prepared by the general procedure by heating for 2.5 hours to afford the desired compound as a dark yellow oil. TFA salt: $^1$H NMR ($CD_3OD$) δ 8.56 (d, 1H, J=5.31 Hz), 8.08 (d, 1H, J=2.02 Hz), 7.74 (d, 1H, J=2.01 Hz), 7.66–7.48 (m, 6H), 7.03–6.95 (m, 2H), 6.79–6.73 (m, 2H), 3.89 (s, 3H). [M+H]+=344.1.

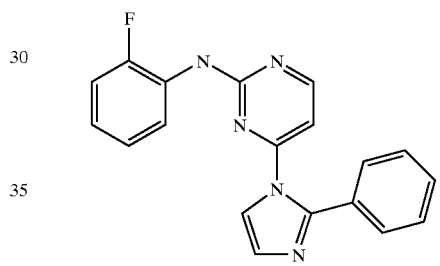

N-(2-fluorophenyl)-4-(2-phenyl-1H-imidazol-1-yl)pyrimidin-2-amine (1-6)

Prepared by the general procedure by heating for 5 hours to afford the desired compound as a dark yellow oil. TFA salt: $^1$H NMR ($CD_3OD$) δ 8.55 (d, 1H, J=5.13 Hz), 8.06 (d, 1H, J=2.01 Hz), 7.75 (d, 1H, J=2.02 Hz), 7.67–7.59 (m, 1H), 7.57 (m, 4H), 7.42 (m, 1H), 7.12–7.06 (m, 2H), 7.03–6.97 (m, 1H), 6.76 (d, 1H, J=5.12 Hz). [M+H]+=332.1.

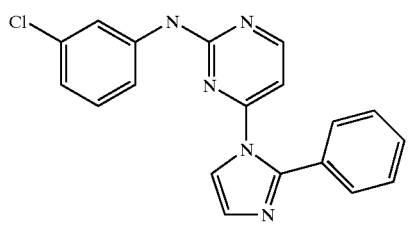

N-(3-chlorophenyl)-4-(2-phenyl-1H-imidazol-1-yl)pyrimidin-2-amine (1-7)

Prepared by the general procedure by heating for 3 hr to afford the desired compound as a yellow oil. TFA salt: $^1$H NMR ($CD_3OD$) δ 8.61 (d, 1H, J=5.19 Hz), 8.11 (d, 1H, J=2.14 Hz), 7.79 (d, 1H, J=2.14 Hz), 7.64–7.52 (m, 6H), 7.25–7.12 (m, 2H), 6.98 (m, 1H), 6.80 (d, 1H, J=5.19 Hz). [M+H]+=348.1018.

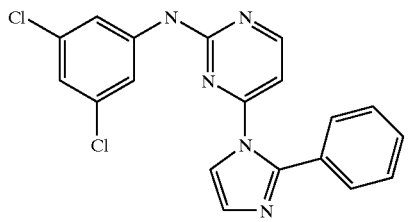

N-(3,5-dichlorophenyl)-4-(2-phenyl-1H-imidazol-1-yl)pyrimidin-2-amine (1-8)

Prepared by the general procedure by heating for 22 hours to afford the desired compound as a yellow oil. TFA salt: $^1$H NMR (CD$_3$OD) δ 8.64 (d, 1H, J=5.19 Hz), 8.12 (d, 1H, J=2.14 Hz), 7.81 (d, 1H, J=1.83 Hz), 7.64–7.49 (m, 7H), 7.02 (t, 1H, J=1.82), 6.85 (d, 1H, J=5.19 Hz). [M+H]+=382.0.

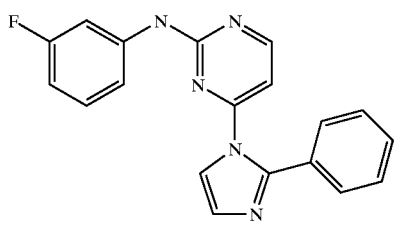

N-(3-fluorophenyl)-4-(2-phenyl-1H-imidazol-1-yl)pyrimidin-2-amine (1-9)

Prepared by the general procedure by heating for 5 hours to afford the desired compound as a yellow oil. TFA salt: $^1$H NMR (CD$_3$OD) δ 8.62 (d, 1H, J=5.12 Hz), 8.13 (d, 1H, J=2.01 Hz), 7.83 (d, 1H, J=2.02 Hz), 7.66–7.45 (m, 5H), 7.30 (d, 1H, J=9.70 Hz), 7.18 (q, 1H, J=8.06 Hz), 7.10–7.04 (m, 1H), 6.83 (d, 1H, J=5.13 Hz), 6.70 (m, 1H). [M+H]+=332.1.

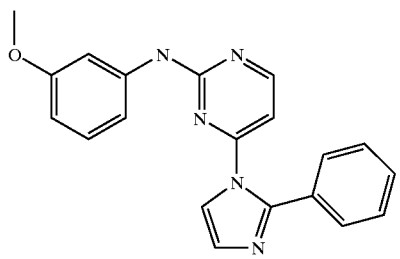

N-(3-methoxyphenyl)-4-(2-phenyl-1H-imidazol-1-yl)pyrimidin-2-amine (1-10)

Prepared by the general procedure by heating for 3 hr to afford the desired compound as a yellow oil. TFA salt: $^1$H NMR (CD$_3$OD) δ 8.53 (d, 1H, J=5.19 Hz), 8.08 (d, 1H, J=1.83 Hz), 7.73 (d, 1H, J=2.13 Hz), 7.65–7.52 (m, 5H), 7.65–7.07 (m, 2H), 6.92 (m, 1H), 6.67 (d, 1H, J=5.19 Hz), 6.59 (m, 1H), 3.77 (s, 3H). [M+H]+=344.1.

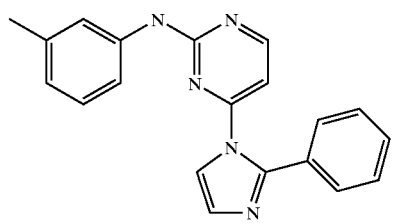

N-(3-methylphenyl)-4-(2-phenyl-1H-imidazol-1-yl)pyrimidin-2-amine (1-11)

Prepared by the general procedure by heating for 3 hr to afford the desired compound as a yellow oil. TFA salt: $^1$H NMR (CD$_3$OD) δ 8.55 (d, 1H, J=5.19 Hz), 8.11 (d, 1H, J=2.14 Hz), 7.82 (d, 1H, J=2.14 Hz), 7.69–7.55 (m, 5H), 7.22 (bs, 1H), 7.15–7.02 (m, 2H), 6.83 (d, 1H, J=7.02 Hz), 6.72 (d, 1H, J=5.19 Hz), 2.28 (s, 3H). [M+H]+=328.1538.

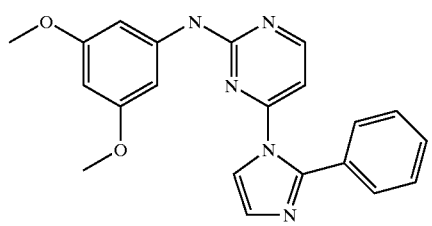

N-(3,5-dimethoxyphenyl)-4-(2-phenyl-1H-imidazol-1-yl)pyrimidin-2-amine (1-12)

Prepared by the general procedure by heating for 3 hr to afford the desired compound as a yellow oil. TFA salt: $^1$H NMR (CD$_3$OD) δ 8.48 (d, 1H, J=5.19 Hz), 8.04 (d, 1H, J=1.83 Hz), 7.66 (d, 1H, J=1.83 Hz), 7.62–7.48 (m, 5H), 7.24–7.06 (m, 1H), 6.82 (d, 1H, J=2.14 Hz), 6.56 (d, 1H, J=5.18 Hz), 6.19 (t, 1H, J=2.44), 3.76 (s, 6H). [M+H]+=374.1.

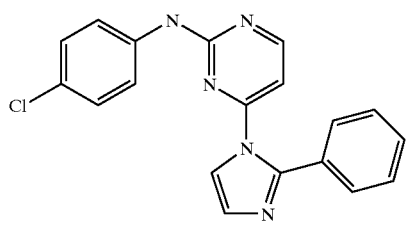

N-(4-chlorophenyl)-4-(2-phenyl-1H-imidazol-1-yl)pyrimidin-2-amine (1-13)

Prepared by the general procedure by heating for hours to afford the desired compound as a yellow oil. TFA salt: $^1$H NMR (CD$_3$OD) δ 8.60 (d, 1H, J=5.19 Hz), 8.12 (d, 1H, J=2.14 Hz), 7.83 (d, 1H, J=2.14 Hz), 7.69–7.55 (m, 5H), 7.31–7.19 (m, 2H), 7.19–7.11 (m, 2H), 6.84 (d, 1H, J=4.88 Hz). [M+H]+=348.1.

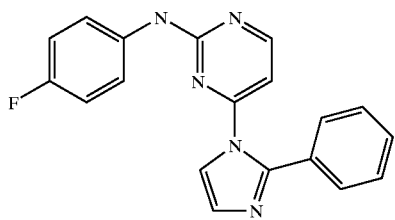

N-(4-fluorophenyl)-4-(2-phenyl-1H-imidazol-1-yl)pyrimidin-2-amine (1-14)

Prepared by the general procedure by heating for 3 hr to afford the desired compound as a yellow oil. TFA salt: $^1$H NMR (CD$_3$OD) δ 8.58 (d, 1H, J=5.19 Hz), 8.11 (d, 1H, J=2.13 Hz), 7.82 (d, 1H, J=2.13 Hz), 7.70–7.56 (m, 5H), 7.30–7.16 (m, 2H), 6.91 (t, 2H, J=8.85 Hz), 6.80 (d, 1H, J=4.89 Hz). [M+H]+=332.1.

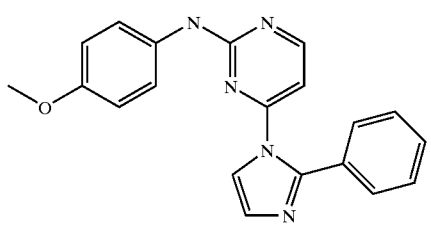

N-(4-methoxyphenyl)-4-(2-phenyl-1H-imidazol-1-yl)pyrimidin-2-amine (1-15)

Prepared by the general procedure by heating for 3 hours to afford the desired compound as a yellow oil. TFA salt: $^1$H NMR (CD$_3$OD) δ 8.52 (d, 1H, J=5.13 Hz), 8.08 (d, 1H, J=1.83 Hz), 7.81 (d, 1H, J=2.01 Hz), 7.70–7.56 (m, 5H), 7.22–7.06 (m, 2H), 7.22–6.68 (m, 3H), 3.76 (s, 3H). [M+H]+=344.1.

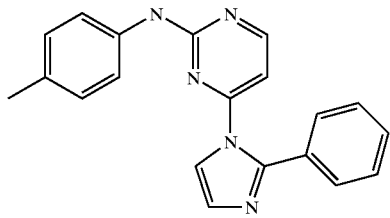

N-(4-methylphenyl)-4-(2-phenyl-1H-imidazol-1-yl)pyrimidin-2-amine (1-16)

Prepared by the general procedure by heating for 3 hours to afford the desired compound as a yellow oil. TFA salt: $^1$H NMR (CD$_3$OD) δ 8.54 (d, 1H, J=5.19 Hz), 8.10 (d, 1H, J=2.14 Hz), 7.81 (d, 1H, J=2.14 Hz), 7.70–7.56 (m, 5H), 7.20–7.06 (m, 2H), 7.00 (m, 2H), 6.74 (d, 1H, J=4.58 Hz), 2.27 (s, 3H). [M+H]+=328.1.

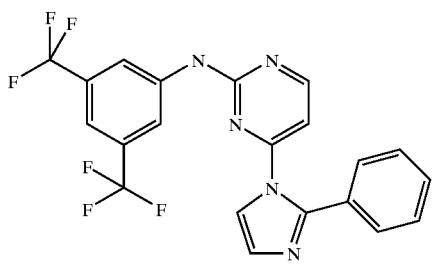

N-[3,5-bis(trifluoromethyl)phenyl]-4-(2-phenyl-1H-imidazol-1-yl)pyrimidin-2-amine (1-17)

Prepared by the general procedure by heating for 24 hours to afford the desired compound as a yellow solid. TFA salt: $^1$H NMR (CD$_3$OD) δ 8.62 (d, 1H, J=5.19 Hz), 8.27 (bs, 2H), 7.07 (d, 1H, J=1.83 Hz), 7.70 (d, 1H, J=1.83 Hz), 7.60–7.46 (m, 6H), 6.73 (d, 1H, J=5.19 Hz). [M+H]+=450.1.

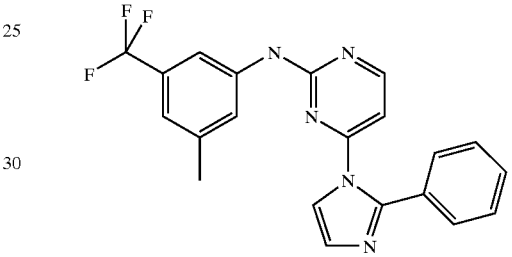

N-[3-methyl-5-(trifluoromethyl)phenyl]-4-(2-phenyl-1H-imidazol-1-yl)pyrimidin-2-amine (1-18)

Prepared by the general procedure by heating for 3 hr to afford the desired compound as a light yellow solid. TFA salt: $^1$H NMR (CD$_3$OD) δ 8.58 (d, 1H, J=5.19 Hz), 8.11 (d, 1H, J=2.13 Hz), 7.82 (bs, 1H), 7.78 (d, 1H, J=2.14 Hz), 7.63–7.48 (m, 6H), 7.12 (bs, 1H), 6.70 (d, 1H, J=5.19 Hz), 2.37 (s, 3H). [M+H]+=396.1431.

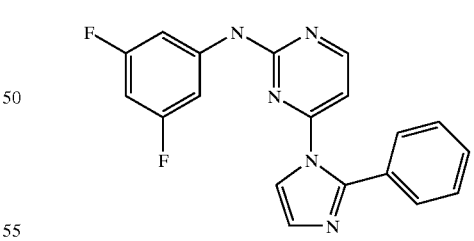

N-(3,5-difluorophenyl)-4-(2-phenyl-1H-imidazol-1-yl)pyrimidin-2-amine (1-19)

Prepared by the general procedure by heating for 24 hours to afford the desired compound as a yellow oil. TFA salt: $^1$H NMR (CD$_3$OD) δ 8.66 (d, 1H, J=5.19 Hz), 8.12 (d, 1H, J=2.13 Hz), 7.81 (d, 1H, J=2.14 Hz), 7.65–7.51 (m, 5H), 7.09 (d, 2H, J=8.54 Hz), 6.88 (d, 1H, J=5.19 Hz), 6.53 (m, 1H). [M+H]+=350.1.

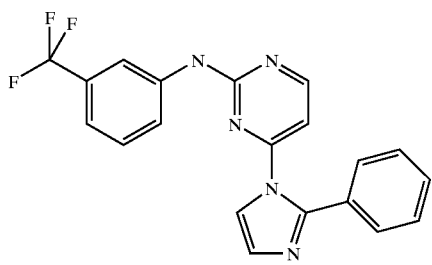

4-(2-phenyl-1H-imidazol-1-yl)-N-[3-(trifluoromethyl)phenyl]pyrimidin-2-amine (1-20)

Prepared by the general procedure by heating for 24 hours to afford the desired compound as a yellow oil. TFA salt: $^1$H NMR (CD$_3$OD) δ 8.63 (d, 1H, J=5.18 Hz), 8.14 (d, 1H, J=2.14 Hz), 7.91 (bs, 1H), 7.84 (d, 1H, J=2.13 Hz), 7.68–7.53 (m, 6H), 7.38 (t, 1H, J=7.93 Hz), 7.30–7.25 (m, 1H), 6.80 (d, 1H, J=5.19 Hz). [M+H]+=382.1.

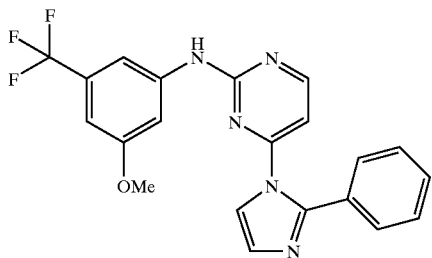

N-[3-Methoxy-5-(trifluoromethyl)phenyl]-4-(2-phenyl-1H-imidazol-1-yl)pyrimidin-2-amine (1-21)

2-(Methylsulfonyl)-4-(2-phenyl-1H-imidazol-1-yl) pyrimidine (1-3, 50 mg, 0.17 mmol), CsF (38 mg, 0.25 mmol) and 3-methoxy-5-trifluoromethyl aniline (79 mg, 0.42 mmol) were taken up in 2-ethoxyethyl ether (1 mL) and heated to 100° C. After 5 hours the mixture was cooled to room temperature and concentrated to dryness. Purification by reverse phase HPLC (5–100% CH$_3$CN/H$_2$O+0.1% TFA) gave a white solid after trituration with Et$_2$O/hexanes: $^1$H-NMR (300 MHz, d$_6$-DMSO) δ 8.35 (m, 1H), 7.95 (m, 1H), 7.45 (m, 10H), 6.18 (m, 1H), 3.80 (s, 3H).

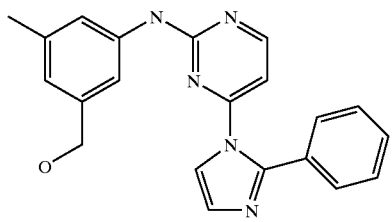

(3-Methyl-5-{[4-(2-phenyl-1H-imidazol-1-yl)pyrimidin-2-yl]amino}phenyl)methanol (1-22)

To a solution of (3-amino-5-methylphenyl)methanol (prepared according to: Behrens, C.; Egholm, M.; Buchardt, O. *Synthesis* 1992, 12, 1235–1236, 750 mg, 5.47 mmol) in CH$_2$Cl$_2$ (25 mL) was added imidazole (447 mg, 6.56 mmol) then TBDMSCl (989 mg, 6.56 mmol) at room temperature. After 72 hours the mixture was diluted with H$_2$O. The layers were separated and the aqueous extracted with CH$_2$Cl$_2$ (2×). The combined organic layers were dried (MgSO$_4$), filtered, and concentrated. Flash column chromatography (20% EtOAc/hexanes) gave 3-({[tert-butyl(dimethyl)silyl]oxy}methyl)-5-methylaniline as a clear oil. $^1$H-NMR (300 MHz, CDCl$_3$) δ 6.58 (s, 1H), 6.50 (s, 1H), 6.40 (s, 1H), 4.60 (s, 2H), 3.60 (bs, 2H), 2.24 (s, 3H).

2-(Methylsulfonyl)-4-(2-phenyl-1H-imidazol-1-yl) pyrimidine (1-3, 200 mg, 0.67 mmol) and 3-({[tert-butyl (dimethyl)silyl]oxy}methyl)-5-methylaniline (502 mg, 2.0 mmol) were combined neat and heated to 130° C. After 1 hour, the mixture was cooled to room temperature and taken up in dry THF (4 mL). To this was added 1 mL HF-pyridine. After 1 hour, the mixture was neutralized with saturated NaHCO$_3$ and extracted with CH$_2$Cl$_2$ (4×). The combined organic layers were dried (MgSO$_4$), filtered, and concentrated. Purification by reverse phase HPLC (5–100% CH$_3$CN/H$_2$O+0.1% TFA) gave an off-white foam after neutralization of the TFA salt with NaHCO$_3$: $^1$H-NMR (500 MHz, CDCl$_3$) δ 8.28 (m, 1H), 7.66 (s, 1H), 7.51 (m, 2H), 7.40 (m, 5H), 7.21 (s, 1H), 6.90 (s, 1H), 6.27 (m, 1H), 4.66 (s, 2H), 2.36 (s, 3H).

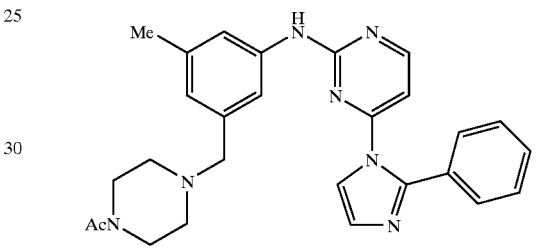

N-{3-[(4-Acetylpiperazin-1-yl)methyl]-5-methylphenyl}-4-(2-phenyl-1H-imidazol-1-yl)pyrimidin-2-amine (1-23)

To a solution of (3-amino-5-methylphenyl)methanol (1.0 g, 7.29 mmol) in CH$_2$Cl$_2$ (30 mL) was added BOC$_2$O (1.75 g, 8.02 mmol) at room temperature. After 24 hours the mixture was concentrated. Flash column chromatography (30% EtOAc/hexanes) gave tert-butyl 3-(hydroxymethyl)-5-methylphenylcarbamate as a white solid. $^1$H-NMR (300 MHz, CDCl$_3$) δ 7.20 (s, 1H), 7.18 (s, 1H), 6.85 (s, 1H), 6.45 (bs, 1H), 4.60 (s, 2H), 3.60 (bs, 2H), 2.32 (s, 3H), 1.50 (s, 9H).

To a suspension of PCC (1.36 g, 6.32 mmol) in CH$_2$Cl$_2$ (10 mL) was added a solution of tert-butyl 3-(hydroxymethyl)-5-methylphenylcarbamate (1.0 g, 4.2 mmol) in CH$_2$Cl$_2$ (10 mL) at room temperature. After 18 hours the mixture was filtered through a pad of Celite® and concentrated. Flash column chromatography (15% EtOAc/hexanes) gave tert-butyl 3-formyl-5-methylphenylcarbamate as a white solid. $^1$H-NM (300 MHz, CDCl$_3$) δ 9.90 (s, 1H), 7.75 (s, 1H), 7.58 (s, 1H), 7.39 (s, 1H), 6.59 (bs, 1H), 2.40 (s, 3H), 1.50 (s, 9H).

To a solution of tert-butyl 3-formyl-5-methylphenylcarbamate (200 mg, 0.85 mmol) and acetylpiperazine (131 mg, 1.02 mmol) in 0.1 mL HOAc and 4 mL dichloroethane was added NaBH(OAc)$_3$ (216 mg, 1.02 mmol) at room temperature. After 2 hours additional acetylpiperazine (131 mg, 1.02 mmol) and NaBH(OAc)$_3$ (216 mg, 1.02 mmol) were added. After 2 hours the mixture was diluted with saturated NaHCO$_3$. The layers were separated and the aqueous extracted with CH$_2$Cl$_2$ (3×). The combined organic layers were dried (MgSO$_4$), filtered, and concentrated. Flash column chromatography (5% MeOH/CH$_2$Cl$_2$) gave tert-butyl 3-[(4-acetylpiperazin-1-yl)methyl]-5-methylphenylcarbamate as a white foam:

$^1$H-NMR (300 MHz, CDCl$_3$) δ 7.15 (s, 1H), 7.09 (s, 1H), 6.81 (s, 1H), 6.44 (s, 1H), 3.62 (t, J=4.88 Hz, 2H), 3.45 (m, 4H), 2.40 (m, 4H), 2.31 (s, 3H), 2.08 (s, 3H), 1.52 (s, 9H).

To a solution of tert-butyl 3-[(4-acetylpiperazin-1-yl) methyl]-5-methylphenylcarbamate (306 mg, 0.88 mmol) in CH$_2$Cl$_2$ (4 mL) was added TFA (4 mL) at room temperature. After 2 hours the mixture was concentrated. The residue was taken up in saturated NaHCO$_3$ and extracted with CH$_2$Cl$_2$ (3×). The combined organic layers were dried (MgSO$_4$), filtered, and concentrated to give 3-[(4-acetylpiperazin-1-yl) methyl]-5-methylaniline as a white solid. $^1$H-NMR (300 MHz, CDCl$_3$) δ 6.52 (s, 1H), 6.48 (s, 1H), 6.43 (s, 1H), 3.62 (m, 4H), 3.45 (m, 2H), 3.39 (s, 2H), 2.40 (m, 4H), 2.25 (s, 3H), 2.08 (s, 3H).

2-(Methylsulfonyl)-4-(2-phenyl-1H-imidazol-1-yl) pyrimidine (1-3, 100 mg, 0.33 mmol) and 3-[(4-acetylpiperazin-1-yl)methyl]-5-methylaniline (240 mg) were combined neat and heated to 130° C. After 2 hours the mixture was cooled to room temperature. Flash column chromatography (gradient, 2–5% MeOH/CH$_2$Cl$_2$) gave the title compound as an off-white foam. $^1$H-NMR (300 MHz, CDCl$_3$) δ 8.26 (d, J=5.5 Hz, 1H), 7.68 (d, J=1.53 Hz, 1H), 7.50 (m, 2H), 7.40 (m, 4H), 7.30 (s, 1H), 7.16 (s, 1H), 6.86 (s, 1H), 6.25 (d, J=5.49 Hz, 1H), 3.64 (t, J=5.19 Hz, 2H), 4H), 3.46 (m, 4H), 2.44 (m, 4H), 2.35 (s, 3H), 2.08 (s, 3H).

N-(3,5-dimethylphenyl)-4-(2-phenyl-1H-imidazol-1-yl)pyrimidin-2-amine (1-24)

2-(Methylsulfonyl)-4-(2-phenyl-1H-imidazol-1-yl) pyrimidine (1-3, 100 mg, 0.33 mmol) and 3,5-dimethylaniline (0.21 ml, 1.66 mmol) were combined neat and heated to 100° C. After 1 hour the mixture was heated to 130° C. After 1 hour, the reaction was partitioned between a pH 5.2 citrate solution and DCM. The aqueous phase was extracted 2× with DCM and the combined organic extracts were dried over Na$_2$SO$_4$, filtered, concentrated and cooled to room temperature. Purification by reverse phase HPLC (5–100% CH$_3$CN/H$_2$O+0.1% TFA) was followed by purification by flash column chromatography (2% MeOH/CH$_2$Cl$_2$) gave the title compound as a white solid. $^1$H-NMR (300 MHz, CDCl$_3$) δ 8.27 (d, J=5.5 Hz, 1H), 7.66 (d, J=1.2 Hz, 1H), 7.53 (m, 2H), 7.40 (m, 4H), 7.18 (m, 2H), 7.11 (s, 1H), 6.74 (s, 1H), 6.25 (d, J=5.5 Hz, 1H), 2.32 (s, 6H). mp=183° C.

SCHEME 2

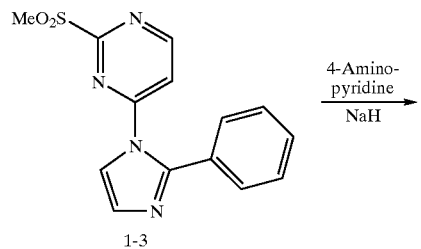

1-3

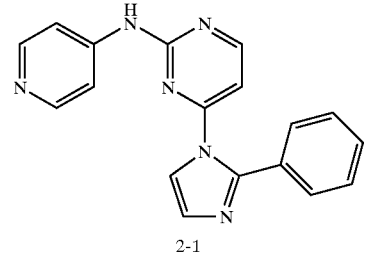

2-1

General Procedure for the Preparation of N-Aryl-4-(2-phenyl-1H-imidazol-1-yl)pyrimidin-2-amines from 2-(Methylsulfonyl)-4-(2-phenyl-1H-imidazol-1-yl)pyrimidine To a solution of the amine (0.17 mmol) in dry THF (1 mL) was added NaH (0.50 mmol) at room temperature. After 20 minutes, 2-(methylsulfonyl)-4-(2-phenyl-1H-imidazol-1-yl) pyrimidine (0.17 mmol) was added all at once. After 18 hours the mixture was quenched with H$_2$O and extracted with CH$_2$Cl$_2$ (3×). The combined organic layers were dried (MgSO$_4$), filtered, and concentrated. The residue was taken up in Et$_2$O and the resulting solid collected by filtration.

4-(2-Phenyl-1H-imidazol-1-yl)-N-pyridin-4-ylpyrimidin-2-amine (2-1)

The title compound was prepared according to the general procedure to give a pale yellow solid. $^1$H-NMR (500 MHz, CDCl$_3$) δ 8.41 (m, 4H), 7.63 (m, 1H), 7.51 (m, 2H), 7.47–7.24 (m, 5H), 6.50 (d, J=5.37 Hz, 1H).

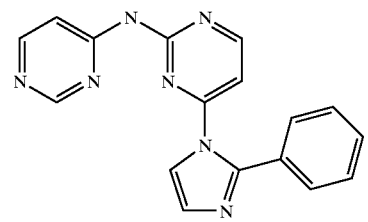

4-(2-Phenyl-1H-imidazol-1-yl)-N-pyrimidin-4-ylpyrimidin-2-amine (2-2)

The title compound was prepared according to the general procedure to give a pale yellow solid. $^1$H-NMR (500 MHz, CDCl$_3$) δ 8.88 (s, 1H), 8.63 (bs, 1H), 8.51 (d, J=5.37 Hz, 1H), 8.44 (d, J=5.85 Hz, 1H), 7.84 (d, J=5.61 Hz, 1H), 7.61 (d, J=1.47 Hz, 1H), 7.51 (m, 2H), 7.41 (m, 3H), 7.30 (d, J=1.47 Hz, 1H), 6.61 (d, J=5.38 Hz, 1H).

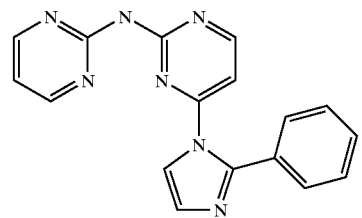

4-(2-Phenyl-1H-imidazol-1-yl)-N-pyrimidin-2-ylpyrimidin-2-amine (2-3)

The title compound was prepared according to the general procedure to give a white solid. $^1$H-NMR (500 MHz, CDCl$_3$) δ 8.65 (d, J=4.88 Hz, 2H), 8.49 (d, J=5.38 Hz, 2H), 8.40 (bs, 1H), 7.75 (d, J=1.47 Hz, 1H), 7.50 (m, 2H), 7.41 (m, 3H), 6.99 (t, J=4.89 Hz, 1H), 6.42 (d, J=5.37 Hz, 1H).

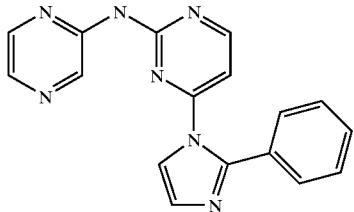

4-(2-Phenyl-1H-imidazol-1-yl)-N-pyrazin-2-ylpyrimidin-2-amine (2-4)

The title compound was prepared according to the general procedure to give an off-white solid. $^1$H-NMR (500 MHz, CDCl$_3$) δ 9.49 (s, 1H), 8.42 (d, J=5.37 Hz, 1H), 8.28 (m, 1H), 7.68 (s, 1H), 7.51 (m, 2H), 7.41 (m, 3H), 7.28 (s, 1H), 6.44 (d, J=5.38 Hz, 1H).

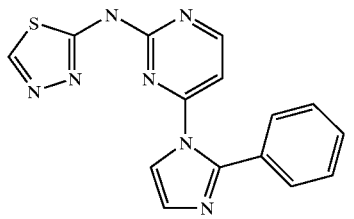

4-(2-Phenyl-1H-imidazol-1-yl)-N-(1,3,4-thiadiazol-2-yl)pyrimidin-2-amine (2-5)

The title compound was prepared according to the general procedure to give a pale yellow solid. $^1$H-NMR (500 MHz, d$_6$-DMSO) δ 8.68 (s, 1H), 8.36 (m, 1H), 7.78 (s, 1H), 7.40 (m, 5H), 7.20 (s, 1H), 6.20 (m, 1H).

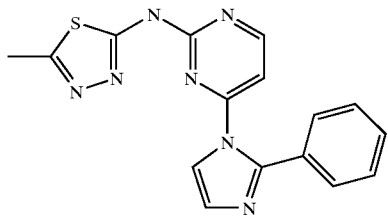

N-(5-Methyl-1,3,4-thiadiazol-2-yl)-4-(2-phenyl-1H-imidazol-1-yl)pyrimidin-2-amine (2-6)

The title compound was prepared according to the general procedure to give an off-white solid. $^1$H-NMR (500 MHz, CDCl$_3$) δ 8.50 (m, 1H), 7.77 (s, 1H), 7.49 (m, 5H), 7.31 (s, 1H), 6.48 (d, J=5.38 Hz, 1H), 2.70 (s, 3H).

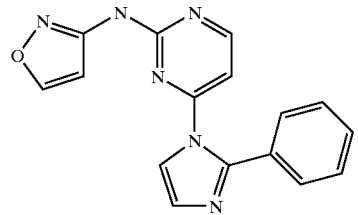

N-Isoxazol-3-yl-4-(2-phenyl-1H-imidazol-1-yl)pyrimidin-2-amine (2-7)

The title compound was prepared according to the general procedure to give a white solid. $^1$H-NMR (500 MHz, CDCl$_3$) δ 8.45 (bs, 1H), 8.44 (d, J=5.37 Hz, 1H), 8.21 (d, J=1.47 Hz, 1H), 7.60 (d, J=1.47 Hz, 1H), 7.49 (m, 2H), 7.39 (m, 3H), 7.28 (d, J=1.22 Hz, 1H), 6.78 (bs, 1H), 6.48 (d, J=5.38 Hz, 1H).

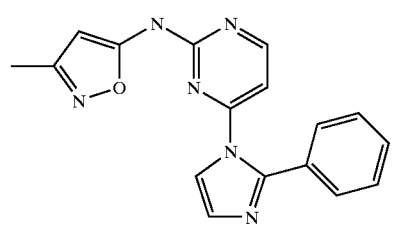

N-(3-Methylisoxazol-5-yl)-4-(2-phenyl-1H-imidazol-1-yl)pyrimidin-2-amine (2-8)

The title compound was prepared according to the general procedure to give an off-white solid. $^1$H-NMR (500 MHz, CDCl$_3$) δ 8.60 (bs, 1H), 8.47 (d, J=5.37 Hz, 1H), 7.61 (s, 1H), 7.49 (m, 2H), 7.40 (m, 3H), 7.29 (s, 1H), 6.54 (d, J=5.13 Hz, 1H), 5.80 (bs, 1H), 2.24 (s, 3H).

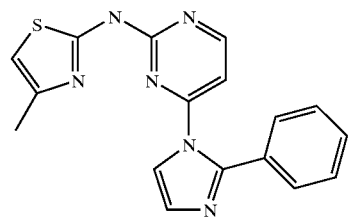

N-(4-Methyl-1,3-thiazol-2-yl)-4-(2-phenyl-1H-imidazol-1-yl)pyrimidin-2-amine (2-9)

The title compound was prepared according to the general procedure to give a tan solid. $^1$H-NMR (500 MHz, CDCl$_3$) δ 8.36 (d, J=5.38 Hz, 1H), 7.85 (bs, 1H), 7.51–7.41 (m, 5H), 7.29 (s, 1H), 6.50 (s, 1H), 6.35 (d, J=5.37 Hz, 1H), 2.38 (s, 3H).

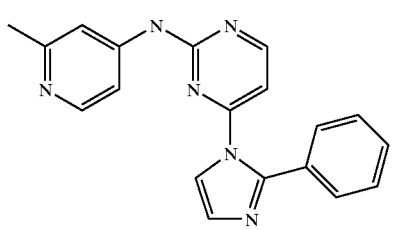

N-(2-Methylpyridin-4-yl)-4-(2-phenyl-1H-imidazol-1-yl)pyrimidin-2-amine (2-10)

The title compound was prepared according to the general procedure except the mixture was heated at 50° C. for 1 hour. After work-up the crude product was purified by reverse phase HPLC (5–100% CH$_3$CN/H$_2$O+0.1% TFA) to give an off-white solid. $^1$H-NMR (500 MHz, d$_6$-DMSO) δ 11.36 (s, 1H), 8.76 (d, J=5.37 Hz, 1H), 8.20 (d, J=7.08 Hz, 1H), 7.86 (d, J=1.71 Hz, 1H), 7.59–7.34 (m, 8H), 7.11 (d, J=5.37 Hz, 1H), 2.5 (s, 3H).

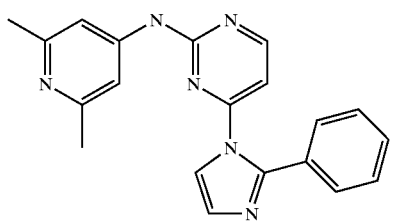

N-(2,6-Dimethylpyridin-4-yl)-4-(2-phenyl-1H-imidazol-1-yl)pyrimidin-2-amine (2-11)

The title compound was prepared according to the general procedure except the mixture was heated at 50° C. for 1 hour to give a tan solid. $^1$H-NMR (500 MHz, d$_4$-MeOH) δ 8.51 (d, J=5.43 Hz, 1H), 7.88 (s, 1H), 7.77 (d, J=1.46 Hz, 1H), 7.48–7.26 (m, 7H), 6.67 (d, J=5.12 Hz, 1H), 6.35 (s, 1H), 2.39 (s, 6H).

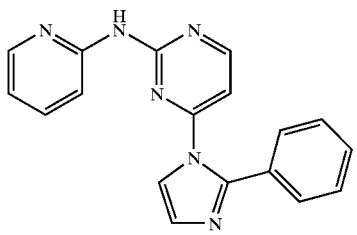

4-(2-Phenyl-1H-imidazol-1-yl)-N-pyridin-2-ylpyrimidin-2-amine (2-12)

To a solution of 2-aminopyridine (31 mg, 0.33 mmol) in dry THF (0.5 mL) was added NaH (32 mg, 1.33 mmol) at room temperature. Once the resulting bubbling had ceased, 2-(methylsulfonyl)-4-(2-phenyl-1H-imidazol-1-yl)pyrimidine (0.100 g, 0.33 mmol) was added all at once. After 1.5 hours the mixture was concentrated in vacuo, diluted with water and the pH of the resulting solution was adjusted to 7 with 1M HCl (aq). The resulting precipitate was filtered and purified by reverse phase HPLC (5–100% CH$_3$CN/H$_2$O+0.1% TFA). $^1$H-NMR (300 MHz, CDCl$_3$) δ 8.44 (d overlapping with s, J=5.4 Hz, 2H), 8.33 (d, J=4.1 Hz, 1H), 7.93 (d, J=8.3 Hz, 1H), 7.55 (m, 4H), 7.40 (m, 3H), 7.33 (m, 1H), 6.95 (dd, J=4.9, 7.1 Hz, 1H), 6.45 (d, J=5.3 Hz, 1H).

SCHEME 3

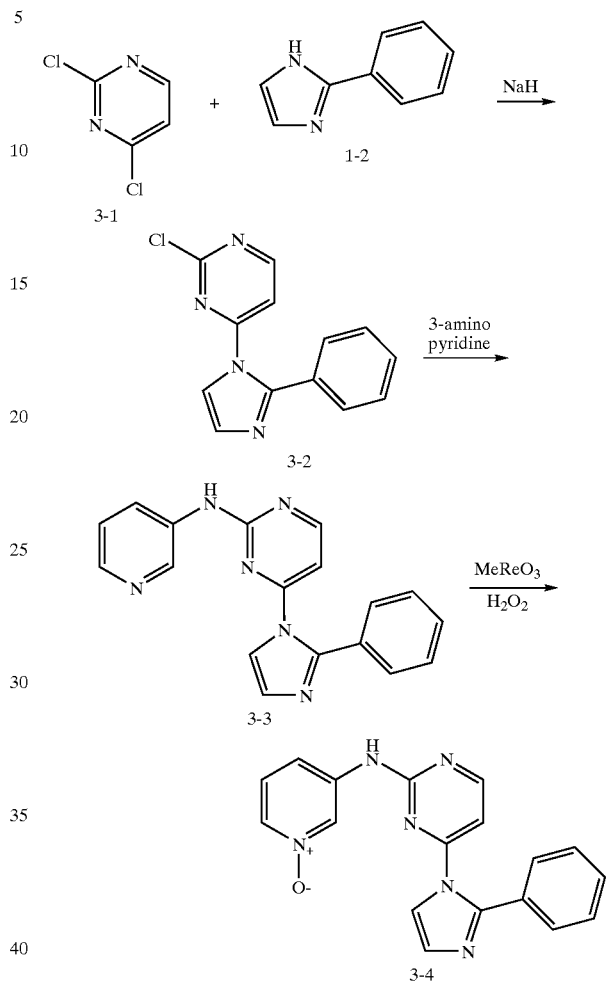

4-(2-Phenyl-1H-imidazol-1-yl)-N-pyridin-3-ylpyrimidin-2-amine (3-3)

To a solution of 2-phenylimidazole (1-2, 484 mg, 3.36 mmol) in dry THF (15 mL) was added NaH (130 mg, 60% dispersion in mineral oil, 3.36 mmol) at room temperature. After gas evolution had ceased, 2,4-dichloropyrimidine (3-1, 0.5 g, 3.36 mmol) was added. The mixture was heated to 50° C. After 18 hours the mixture was cooled to room temperature, quenched with saturated NH$_4$Cl, and extracted with EtOAc (3×). The combined organic layers were dried (MgSO$_4$), filtered, and concentrated. Flash column chromatography (50% EtOAc/hexanes) gave 2-chloro-4-(2-phenyl-1H-imidazol-1-yl)pyrimidine as a gum. $^1$H-NMR (300 MHz, CDCl$_3$) δ 8.40 (d, J=5.38 Hz, 1H), 7.80 (s, 1H), 7.45 (m, 5H), 7.25 (s, 1H), 6.68 (d, J=5.38 Hz, 1H).

To a solution of 2-chloro-4-(2-phenyl-1H-imidazol-1-yl)pyrimidine (3-2, 50 mg, 0.2 mmol), 3-aminopyridine (22 mg, 0.23 mmol), NaOtBu (26 mg, 0.27 mmol), 2-biphenyl-di-tert-butylphosphine (5 mg, 0.02 mmol) was added Pd(OAc)$_2$ (2 mg, 0.01 mmol) at room temperature. After 72 hours the mixture was diluted with H$_2$O and extracted with EtOAc (3×). The combined organic layers were dried (MgSO$_4$), filtered, and concentrated. Flash column chromatography (gradient, 3–10% MeOH/CH$_2$Cl$_2$) gave the title compound as an off-white solid after trituration with Et$_2$O/hexanes. $^1$H-NMR (500 MHz, CDCl$_3$) δ 8.62 (d, J=1.95 Hz, 1H), 8.33 (d, J=5.37 Hz, 1H), 8.29 (d, J=4.40 Hz, 1H), 7.91 (d, J=7.08 Hz, 1H), 7.61 (d, J=1.22 Hz, 1H), 7.50 (m, 2H), 7.41 (m, 3H), 7.21 (m, 2H), 6.40 (d, J=5.37 Hz, 1H).

N-(1-Oxidopyridin-3-yl)-4-(2-phenyl-1H-imidazol-1-yl)pyrimidin-2-amine (3-4)

To a solution of 4-(2-phenyl-1H-imidazol-1-yl)-N-pyridin-3-ylpyrimidin-2-amine (3-3, 0.17 mmol) in CH$_2$Cl$_2$ (1 mL) was added MeReO$_3$ (1 mg) then 30% H$_2$O$_2$ (0.05 mL) with vigorous stirring at room temperature. After 18 hrours additional MeReO$_3$ (1 mg) and 30% H$_2$O$_2$ (0.05 mL) were added. After 18 hours the mixture was concentrated. Purification by reverse phase HPLC (5–100% CH$_3$CN/H$_2$O+0.1% TFA) gave the title compound as a tan solid after trituration with Et$_2$O. $^1$H-NMR (500 MHz, d$_6$-DMSO) δ 10.38 (s, 1H), 8.68 (d, J=5.13 Hz, 1H), 8.57 (s, 1H), 7.99 (s, 1H), 7.87 (d, J=5.86 Hz, 1H), 7.55 (m, 6H), 7.27 (bs, 1H), 7.20 (s, 1H), 6.86 (d, J=4.64 Hz, 1H).

SCHEME 4

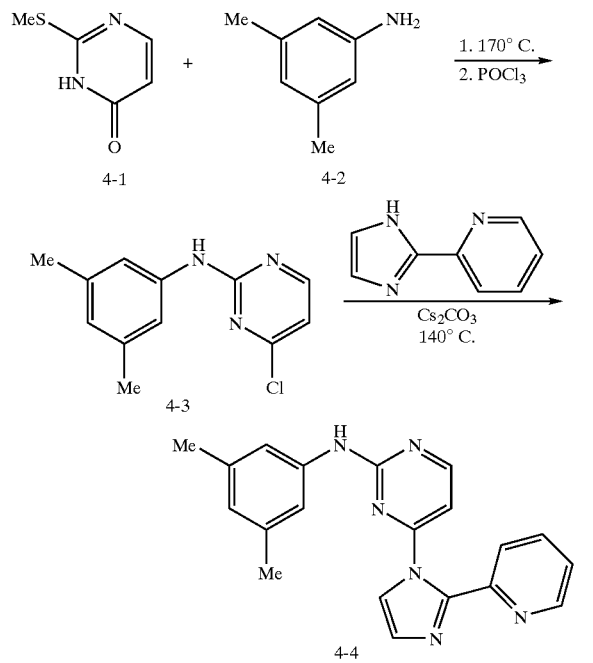

4-Chloro-N-(3,5-dimethylphenyl)pyrimidin-2-amine (4-3)

2-(Methylthio)pyrimidin-4(3H)-one (4-1, 2.00 g, 14.1 mmol) and 3,5-dimethylaniline (2.10 ml, 16.9 mmol) were stirred in 14 ml of 2-ethoxyethyl ether and the resulting solution was heated to 170° C. After 3 days the reaction was concentrated in vacuo. The residue was diluted with 95:5 DCM/MeOH. The solid, which did not dissolve, was filtered to afford a sample of pure 2-(3,5-dimethylphenylamino)-3H-pyrimidin-4-one. The filtrate was concentrated in vacuo and the residue was triturated with ether. The mixture was filtered and the solid was washed with ether. The solid sample was combined with the previous precipitate to afford 2-(3,5-dimethyl-phenylamino)-3H-pyrimidin-4-one.

2-(3,5-Dimethyl-phenylamino)-3H-pyrimidin-4-one (2.01 g, 9.34 mmol) was dissolved in POCl$_3$ (8.70 ml, 93.4 mmol) and the mixture was heated to 100° C. in a round bottom flask equipped with a reflux condenser and a drying tube. After 5 hours the reaction was cooled to room temperature and concentrated in vacuo. The residue was quenched by the addition of sat NaHCO$_3$ (aq) and was extracted 3× with DCM. The combined organic extracts were dried over Na$_2$SO$_4$, filtered and concentrated. The residue was purified by flash column chromatography (dissolved sample in DCM, eluted with 85:15 hexane/EtOAc) to afford 4-chloro-N-(3,5-dimethylphenyl)pyrimidin-2-amine (4-3).

General Procedure for the Preparation of N-(3,5-Dimethylphenyl)-4-(2-substituted-1H-imidazol-1-yl)pyrimidin-2-amines from 4-Chloro-N-(3,5-dimethylphenyl)pyrimidin-2-amine 4-Chloro-N-(3,5-dimethylphenyl)pyrimidin-2-amine (0.21 mmol), the imidazole (0.26 mmol) and Cs$_2$CO$_3$ (0.43 mmol) were combined in dry N,N-dimethylacetamide (1 mL) and heated to 140° C. After 1–18 hours the mixture was cooled to room temperature, neutralized with AcOH, and concentrated.

N-(3,5-Dimethylphenyl)-4-(2-pyridin-2-yl-1H-imidazol-1-yl)pyrimidin-2-amine (4-4)

The title compound was prepared according to the general procedure to give a white solid after purification by flash column chromatography (100% EtOAc): $^1$H-NMR (500 MHz, d$_6$-DMSO) δ 9.73 (s, 1H), 8.69 (d, J=2.44 Hz, 1H), 8.59 (d, J=5.38 Hz, 1H), 8.52 (m, 1H), 7.82 (m, 2H), 7.40 (m, 2H), 7.30 (s, 1H), 7.04 (bs, 2H), 6.79 (d, J=5.13 Hz, 1H), 6.55 (s, 1H), 2.13 (s, 6H).

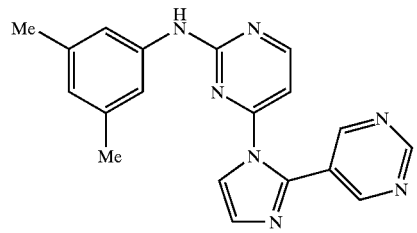

N-(3,5-Dimethylphenyl)-4-(2-pyrimidin-5-yl-1H-imidazol-1-yl)pyrimidin-2-amine (4-5)

To a solution of pyrimidine-5-carboxaldehyde (1.0 g, 9.25 mmol) in concentrated NH$_4$OH (10 mL) was added glyoxal (2 mL, 40% in H$_2$O) at room temperature. After 18 hours the mixture was concentrated to dryness. Flash column chromatography (5% MeOH/CH$_2$Cl$_2$) gave 5-(1H-imidazol-2-yl)pyrimidine as an off-white solid after trituration with cold EtOAc. $^1$H-NMR (500 MHz, d$_6$-DMSO) δ 12.95 (bs, 1H), 9.30 (s, 2H), 9.15 (s, 1H), 7.30 (s, 2H).

The TFA salt of the title compound was prepared according to the general procedure to give a pale yellow solid after purification by reverse phase HPLC (5–100% CH$_3$CN/H$_2$O+0.1% TFA). $^1$H-NMR (500 MHz, d$_4$-MeOH) δ 8.93 (s, 1H), 8.84 (s, 1H), 8.54 (d, J=5.38 Hz, 1H), 7.87 (d, J=1.71 Hz, 1H), 7.37 (d, J=1.47 Hz, 1H), 6.92 (m, 4H), 6.63 (s, 1H), 2.20 (s, 6H).

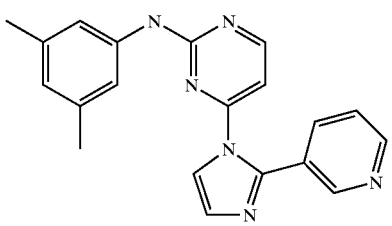

N-(3,5-Dimethylphenyl)-4-(2-pyridin-3-yl-1H-imidazol-1-yl)pyrimidin-2-amine (4-6)

To a solution of pyridine-3-carboxaldehyde (1.0 g, 9.33 mmol) in concentrated NH$_4$OH (10 mL) was added glyoxal (2.1 mL, 40% in H$_2$O) at room temperature. After 18 hours the mixture was concentrated to dryness. Flash column chromatography (gradient, 3–10% MeOH/CH$_2$Cl$_2$) gave 3-(1H-imidazol-2-yl)pyridine as an off-white solid after trituration with cold EtOAc. $^1$H-NMR (300 MHz, d$_4$-MeOH) δ 9.05 (m, 1H), 8.50 (m, 1H), 8.28 (m, 1H), 7.55 (m, 1H), 7.20 (s, 2H).

The title compound was prepared according to the general procedure to give a white solid after purification by flash column chromatography (gradient, 0–5% EtOH/EtOAc). $^1$H-NMR (500 MHz, CDCl$_3$) δ 8.76 (d, J=1.7 Hz, 1H), 8.60 (d, J=3.66 Hz, 1H), 8.36 (d, J=5.38 Hz, 1H), 7.85 (d, J=7.81 Hz, 1H), 7.61 (s, 1H), 7.31 (m, 2H), 7.09 (s, 2H), 6.73 (s, 1H), 6.36 (d, J=5.37 Hz, 1H), 2.30 (s, 6H).

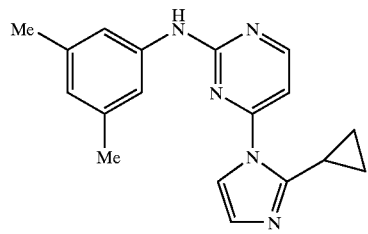

4-(2-Cyclopropyl-1H-imidazol-1-yl)-N-(3,5-dimethylphenyl)pyrimidin-2-amine (4-7)

To a solution of cyclopropyl carboxaldehyde (1.0 g, 14.27 mmol) in concentrated NH$_4$OH (10 mL) was added glyoxal (3 mL, 40% in H$_2$O) at 0° C. The mixture was allowed to warm as the bath warmed to room temperature. After 4 hours the resulting grey solid was collected by filtration, washed with H$_2$O, and dried in vacuo to give 2-cyclopropyl-1H-imidazole. $^1$H-NMR (300 MHz, CDCl$_3$) δ 6.95 (s, 2H), 1.95 (m, 1H), 0.98 (m, 4H).

The TFA salt of the title compound was prepared according to the general procedure to give an off-white solid after purification by reverse phase HPLC (5–100% CH$_3$CN/H$_2$O+0.1% TFA). $^1$H-NMR (500 MHz, d$_6$-DMSO) δ 9.88 (s, 1H), 8.73 (d, J=5.37 Hz, 1H), 7.96 (d, J=1.95 Hz, 1H), 7.49 (s, 1H), 7.34 (s, 2H), 7.12 (d, J=5.37 Hz, 1H), 6.72 (s, 1H), 2.78 (m, 1H), 2.23 (s, 6H), 1.05 (m, 4H).

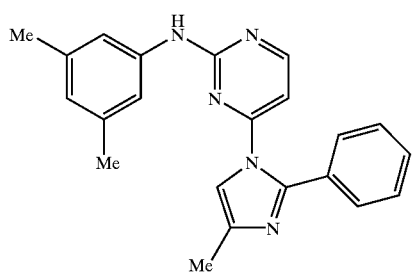

N-(3,5-Dimethylphenyl)-4-(4-methyl-2-phenyl-1H-imidazol-1-yl)pyrimidin-2-amine (4-8)

The TFA salt of the title compound was prepared according to the general procedure to give an orange solid after purification by reverse phase HPLC (5–100% CH$_3$CN/H$_2$O+0.1% TFA). $^1$H-NMR (500 MHz, d$_4$-MeOH) δ 8.48 (m, 1H), 7.74 (s, 1H), 7.56 (m, 5H), 7.07 (s, 2H), 6.67 (s, 1H), 6.61 (d, J=5.13 Hz, 1H), 2.44 (s, 3H), 2.24 (s, 6H).

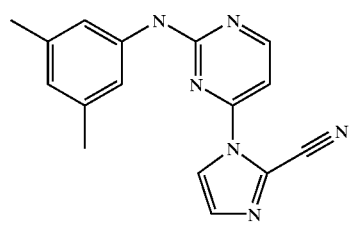

1-{2-[(3,5-Dimethylphenyl)amino]pyrimidin-4-yl}-1H-imidazole-2-carbonitrile (4-9)

To a suspension of imidazole-2-carboxaldehyde (500 mg, 5.2 mmol) in MeOH (10 mL) was added 0.55 mL 50% hydroxylamine in H$_2$O at RT. DMF (10 mL) was added to aid solubility. After 18 hours the mixture was concentrated. Flash column (5% MeOH/CH$_2$Cl$_2$) gave 1H-imidazole-2-carbaldehyde oxime as an off-white foam. $^1$H-NMR (300 MHz, d$_4$-MeOH) indicated a 3:1 mixture of isomers.

To a solution of 1H-imidazole-2-carbaldehyde oxime (606 mg, 5.45 mmol) in EtOAc (20 mL) was added TFAA (2.3 mL, 16.37 mmol) slowly at 0° C. After 90 minutes additional TFAA (2.3 mL) was added and stirring continued. After 30 minutes, the mixture was concentrated. The residue was taken up in saturated NaHCO$_3$ and extracted with EtOAc (3×). The combined organic layers were dried (MgSO$_4$), filtered, and concentrated. Flash column chromatography (5% MeOH/CH$_2$Cl$_2$) gave 1H-imidazole-2-carbonitrile as a white solid. $^1$H-NMR (300 MHz, d$_4$-MeOH) δ 7.30 (s, 2H).

The title compound was prepared according to the general procedure to give a tan solid after trituration with Et$_2$O. $^1$H-NMR (300 MHz, d$_6$-DMSO) δ 9.89 (s, 1H), 8.73 (d, J=5.80 Hz, 1H), 8.25 (s, 1H), 7.48 (s, 1H), 7.40 (s, 2H), 7.20 (d, J=5.18 Hz, 1H), 6.66 (s, 1H), 2.26 (s, 6H).

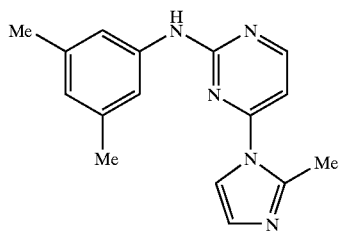

N-(3,5-Dimethylphenyl)-4-(2-methyl-1H-imidazol-1-yl)pyrimidin-2-amine (4-10)

The TFA salt of the title compound was prepared according to the general procedure to give an off-white solid after purification by reverse phase HPLC (5–100% CH$_3$CN/H$_2$O+0.1% TFA). $^1$H-NMR (300 MHz, d$_6$-DMSO) δ 9.91 (s, 1H), 8.73 (d, J=5.19 Hz, 1H), 8.09 (d, J=1.83 Hz, 1H), 7.64 (s, 1H), 7.31 (s, 2H), 7.20 (d, J=5.19 Hz, 1H), 6.70 (s, 1H), 2.82 (s, 3H), 2.26 (s, 6H).

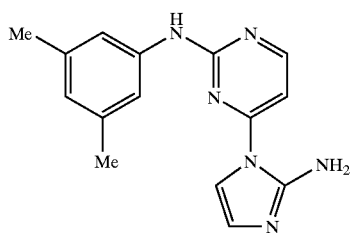

4-(2-Amino-1H-imidazol-1-yl)-N-(3,5-dimethylphenyl)pyrimidin-2-amine (4-11)

The TFA salt of the title compound was prepared according to the general procedure to give a tan solid after purification by reverse phase HPLC (5–100% CH$_3$CN/H$_2$O+0.1% TFA). $^1$H-NMR (300 MHz, d$_6$-DMSO) δ 12.51 (bs, 1H), 9.97 (s, 1H), 9.04 (bs, 2H), 8.66 (d, J=5.50 Hz, 1H), 7.83 (s, 1H), 7.29 (s, 2H), 7.23 (s, 1H), 6.71 (s, 1H), 2.27 (s, 6H).

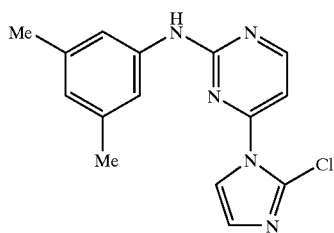

4-(2-Chloro-1H-imidazol-1-yl)-N-(3,5-dimethylphenyl)pyrimidin-2-amine (4-12)

The title compound was prepared according to the general procedure. Purification by flash column chromatography (dissolved sample in DCM, eluted with 1:1 hex/EA). $^1$H NMR (300 MHz, CDCl$_3$) δ 8.54 (d, J=5.5 Hz, 1H), 7.64 (d, J=1.8 Hz, 1H), 7.28 (bs, 1H), 7.24 (s, 2H), 7.13 (d, J=5.5 Hz, 1H), 7.08 (d, J=1.8 Hz, 1H), 6.76 (s, 1H), 2.34 (s, 6H).

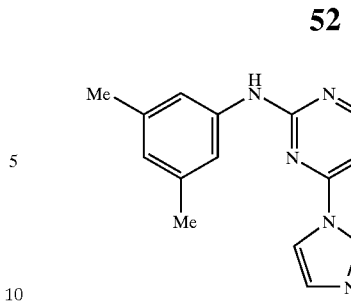

N-(3,5-Dimethylphenyl)-4-[2-(3-fluorophenyl)-1H-imidazol-1-yl]pyrimidin-2-amine (4-13)

4-(2-Chloro-1H-imidazol-1-yl)-N-(3,5-dimethylphenyl) pyrimidin-2-amine (4-12, 36 mg, 0.12 mmol), 3-fluorophenylboronic acid (19 mg, 0.13 mmol), palladium (II)acetate (1.3 mg, 0.01 mmol), triphenylphosphine (4.7 mg, 0.02 mmol) and sodium carbonate (15 mg, 0.14 mmol) were stirred in 1.6 mL of 3:1 nPrOH/water. The reaction was heated at 100° C. for 24 hours. The reaction was concentrated and dissolved in 0.5 ml DMSO and was purified by reverse phase HPLC (5–100% CH$_3$CN/H$_2$O+0.1% TFA) to afford the title compound as a TFA salt. $^1$H NMR (300 MHz, CDCl$_3$) δ 8.36 (d, J=5.5 Hz, 1H), 7.67 (s, 1H), 7.55 (s, 1H), 7.35 (m, 1H), 7.23 (m, 1H), 7.09 (s, 2H), 6.80 (s, 1H), 6.37 (d, J=5.5 Hz, 1H), 2.36 (s, 6H).

SCHEME 5

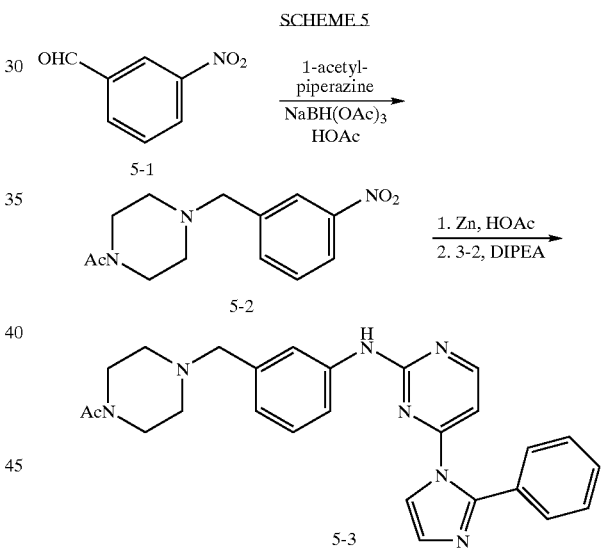

N-{3-[(4-acetylpiperazin-1-yl)methyl]phenyl}-4-(2-phenyl-1H-imidazol-1-yl)pyrimidin-2-amine (5-3)

3-Nitrobenzaldehyde (2.04 g, 13.5 mmol) was dissolved in 50 ml 1,2-dichloroethane. 1-Acetylpiperazine 1.90 g, 14.9 mmol) and sodium triacetoxyborohydride (3.15 g, 14.9 mmol) were added followed by the addition of 0.100 ml of acetic acid. The reaction was allowed to proceed overnight (18 hours) and was then quenched with half-saturated NaHCO$_3$ (aq). The mixture was extracted 3× with DCM and the organic extracts were dried over Na$_2$SO$_4$, filtered and concentrated. The residue was purified by flash column chromatography (eluting with 95:5 DCM/MeOH) to afford 1-acetyl-4-(3-nitrobenzyl)piperazine (5-2). $^1$H NMR (300 MHz, CDCl$_3$) δ 8.22 (s, 1H), 8.13 (dd, J=1.2, 8.3 Hz, 1H), 7.66 (d, J=7.6 Hz, 1H), 7.50 (t, J=7.9 Hz, 1H), 3.63 (t, J=5.2 Hz, 2H), 3.61 (s, 2H), 3.48 (t, J=4.8 Hz, 2H), 2.44 (m, 4H), 2.08 (s, 3H).

1-Acetyl-4-(3-nitrobenzyl)piperazine (5-2, 1.02 g, 3.87 mmol) was dissolved in 10 ml of acetic acid. Zinc powder (1.27 g, 19.4 mmol) was added and the reaction was heated to reflux. After 7 hours the reaction was cooled, filtered through celite and washed with HOAc. The filtrate was concentrated in vacuo and the resulting residue was diluted with saturated NaHCO$_3$ (aq). The mixture was extracted 3× with EtOAc and the combined organic extracts were dried over Na$_2$SO$_4$, filtered and concentrated. Purification by flash column chromatography (gradient 95:5 to 90:10 DCM/MeOH) provided as the major product the hydrazine by-product and as a minor product the desired 3-[(4-acetylpiperazin-1-yl)methyl]aniline.

2-Chloro-4-(2-phenyl-1H-imidazol-1-yl)pyrimidine (56 mg, 0.22 mmol) and 3-[(4-acetylpiperazin-1-yl)methyl] aniline (142 mg, 0.61 mmol) were mixed and heated neat to 100° C. After 2 hours the reaction was heated to 120° C. for 1 hour then to 140° C. for 1 hour. N,N-di-iso-propylethylamine (0.076 ml, 0.44 mol) was added and the reaction was heated for an additional 1.5 hours. The reaction was cooled, diluted with DMSO and directly purified by reverse phase HPLC (5–100% CH$_3$CN/H$_2$O+0.1% TFA) to afford the title compound. $^1$H NMR (300 MHz, CDCl$_3$) δ 8.29 (d, J=5.2 Hz, 1H), 7.67 (d, J=1.5 Hz, 1H), 7.52 (m, 3H), 7.41 (m, 4H), 7.25 (m, 2H), 7.02 (d, J=7.8 Hz, 1H), 6.30 (d, J=5.1 Hz, 1H), 3.63 (t, J=5.5 Hz, 2H), 3.52 (s, 2H), 3.47 (m, 2H), 2.45 (m, 4H), 2.08 (s, 3H).

Assays

The compounds of the instant invention described in the Examples were tested by the assays described below and were found to have kinase inhibitory activity. Other assays are known in the literature and could be readily performed by those of skill in the art (see, for example, Dhanabal et al., Cancer Res. 59:189–197; Xin et al., J. Biol. Chem. 274:9116–9121; Sheu et al., Anticancer Res. 18:4435–4441; Ausprunk et al., Dev. Biol. 38:237–248; Gimbrone et al., J. Natl. Cancer Inst. 52:413–427; Nicosia et al., In Vitro 18:538–549).

VEGF/KDR Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash Buffer 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.

10× Reaction Buffer 200 mM Tris, pH 7.4, 1.0 M NaCl, 50 mM MnCl$_2$, 10 mM DTT and 5 mg/mL bovine serum albumin (Sigma).

Enzyme Dilution Buffer 50 mM Tris, pH 7.4, 0.1 M NaCl, 1 mM DTT, 10% glycerol, 100 mg/mL BSA.

10× Substrate

750 μg/mL poly (glutamic acid, tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.

2. Add 35 μl of reaction mix containing 5 μl of 10× reaction buffer, 5 μl 25 mM ATP/10 μCi [$^{33}$P]ATP (Amersham), and 5 μl 10× substrate.

3. Start the reaction by the addition of 10 μl of KDR (25 nM) in enzyme dilution buffer.

4. Mix and incubate at room temperature for 15 minutes.

5. Stop by the addition of 50 μl stop solution.

6. Incubate for 15 minutes at 4° C.

7. Transfer a 90 μl aliquot to filter plate.

8. Aspirate and wash 3 times with wash solution.

9. Add 30 μl of scintillation cocktail, seal plate and count in a Wallac Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs

HUVECs frozen as primary culture isolates are obtained from Clonetics Corp. Cells are maintained in Endothelial Growth Medium (EGM; Clonetics) and are used for mitogenic assays at passages 3–7.

Culture Plates

NUNCLON 96-well polystyrene tissue culture plates (NUNC #167008).

Assay Medium

Dulbecco's modification of Eagle's medium containing 1 g/mL glucose (low-glucose DMEM; Mediatech) plus 10% (v/v) fetal bovine serum (Clonetics).

Test Compounds

Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors

Solutions of human $VEGF_{165}$ (500 ng/mL; R&D Systems) and bFGF (10 ng/mL; R&D Systems) are prepared in Assay Medium.

10× [$^3$H]Thymidine

[Methyl-3H]Thymidine (20 Ci/mmol; Dupont-NEN) is diluted to 80 µCi/mL in low-glucose DMEM.

Cell Wash Medium

Hank's balanced salt solution (Mediatech) containing 1 mg/mL bovine serum albumin (Boehringer-Mannheim).

Cell Lysis Solution

1 N NaOH, 2% (w/v) $Na_2CO_3$.

Method

1. HUVEC monolayers maintained in EGM are harvested by trypsinization and plated at a density of 4000 cells per 100 µL Assay Medium per well in 96-well plates. Cells are growth-arrested for 24 hours at 37° C. in a humidified atmosphere containing 5% $CO_2$.

2. Growth-arrest medium is replaced by 100 µL Assay Medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

3. After the 2-hour pretreatment period, cells are stimulated by addition of 10 µL/well of either Assay Medium, 10× VEGF solution or 10× bFGF solution. Cells are then incubated at 37° C./5% $CO_2$.

4. After 24 hours in the presence of growth factors, 10× [$^3$H]Thymidine (10 µL/well) is added.

5. Three days after addition of [$^3$H]thymidine, medium is removed by aspiration, and cells are washed twice with Cell Wash Medium (400 µL/well followed by 200 µL/well). The washed, adherent cells are then solubilized by addition of Cell Lysis Solution (100 µL/well) and warming to 37° C. for 30 minutes. Cell lysates are transferred to 7-mL glass scintillation vials containing 150 µL of water. Scintillation cocktail (5 mL/vial) is added, and cell-associated radioactivity is determined by liquid scintillation spectroscopy.

Based upon the foregoing assays the compounds of Formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with $IC_{50}$ values between 0.01–5.0 µM. These compounds also show selectivity over related tyrosine kinases (e.g., FGFR1 and the Src family; for relationship between Src kinases and VEGFR kinases, see Eliceiri et al., Molecular Cell, Vol. 4, pp.915–924, December 1999).

EREKA Kinase Assay (EGFR Assay)

Method:

1. Dilute inhibitors (account for the final dilution into the assay, 1:20)
2. Prepare the appropriate amount of reaction mix at room temperature.
   10× Buffer (20 mM Tris pH 7.4/0.1 M NaCl/1 mM DTT final)
   0.1M $MnCl_2$ (5 mM final)
   pEY substrate (75 µg/ml)
   ATP/[$^{33}$P]ATP (2.5 µM/1 µCi final)
   BSA (500 µg/ml final)
   $Na_3VO_4$ (500 µM final)
3. Add 5 µl of the diluted inhibitor to the reaction mix. (Final volume of 5 µl in 50% DMSO) Positive control wells— add blank DMSO (50%).
4. Add 35 µl of the reaction mix to each well of a 96 well plate.
5. Dilute enzyme (1:100) into enzyme dilution buffer (keep at 4° C.).
6. Add 10 µl of the diluted enzyme to each well and mix. Negative control wells—add 10 µl 0.5 M EDTA per well instead (final 100 mM).
7. Incubate at room temperature for 60 minutes.
8. Stop by the addition of an equal volume (50 µl) of 30% TCA/0.1M Na pyrophosphate.
9. Incubate for 15 minutes to allow precipitation.
10. Transfer to Millipore filter plate.
11. Wash 3× with 15% TCA/0.1M Na pyrophosphate (125 µl per wash).
12. Allow to dry under vacuum for 2–3 minutes.
13. Dry in hood for ~20 minutes.
14. Assemble Wallac Millipore adapter and add 50 µl of scintillant to each well and count.

Alternative Method:

1. Dilute inhibitors (account for the final dilution into the assay, 1:20)
2. Prepare the appropriate amount of reaction mix at room temperature.
   10× Buffer (20 mM Tris pH 7.4/0.1 M NaCl/1 mM DTT final)
   0.1M $MnCl_2$ (5 mM final)
   pEY substrate (75 µg/ml)
   ATP/[$^{33}$P]ATP (2.5 µM/1 µCi final)
   BSA (500 µg/ml final)
3. Add 5 µl of the diluted inhibitor to the reaction mix. (Final volume of 5 µl in 50% DMSO) Positive control wells— add blank DMSO (50%).
4. Add 35 µl of the reaction mix to each well of a 96 well plate.
5. Dilute enzyme into enzyme dilution buffer (keep at 4° C.).
6. Add 10 µl of the diluted enzyme to each well and mix (5 nM final). Negative control wells—add 10 µl 0.5 M EDTA per well instead (final 100 mM).
7. Incubate at room temperature for 30 minutes.
8. Stop by the addition of an equal volume (50 µl) of 30% TCA/0.1M Na pyrophosphate.
9. Incubate for 15 minutes to allow precipitation.
10. Transfer to Millipore filter plate.
11. Wash 3× with 15% TCA/0.1M Na pyrophosphate (125 µl per wash).
12. Allow to dry under vacuum for 2–3 minutes.
13. Dry in hood for ~20 minutes.
14. Assemble Wallac Millipore adapter and add 50 µl of scintillant to each well and count.

SRC Assay
SRCKA (Mg++) Kinase Assay
1. Dilute inhibitors (account for the final dilution into the assay, 1:20).
2. Prepare the appropriate amount of reaction mix at room temperature.
   10× Buffer (20 mM Tris pH 7.4/0.1 M NaCl/1 mM DTT final)
   0.1M MgCl$_2$ (5 mM final)
   pEY substrate (75 μg/ml)
   ATP/[$^{33}$P]ATP (24 μM/3 μCi final)
   BSA (500 μg/ml final)
3. Add 5 μl of the diluted inhibitor to the reaction mix. (Final volume of 5 μl in 50% DMSO) Positive control wells—add blank DMSO (50%).
4. Add 35 μl of the reaction mix to each well of a 96 well plate.
5. Dilute enzyme (1:22) into enzyme dilution buffer (keep at 4° C.). Final enzyme conc.=0.44 nM.
6. Add 10 μl of the diluted enzyme to each well and mix. Negative control wells—add 10 μl 0.5 M EDTA per well instead (final 100 mM)
7. Incubate at room temperature for 30 minutes.
8. Stop by the addition of an equal volume (50 μl) of 30% TCA/0.1M Na pyrophosphate.
9. Incubate for 15 minutes to allow precipitation.
10. Transfer to Millipore filter plate.
11. Wash 3× with 15% TCA/0.1M Na pyrophosphate (125 μl per wash).
12. Allow to dry under vacuum for 2–3 minutes.
13. Dry in hood for ~20 minutes.
14. Assemble Wallac Millipore adapter and add 50 μl of scintillant to each well and count.

Alternative Method:
SRCKA (Mn++) Kinase Assay
1. Dilute inhibitors (account for the final dilution into the assay, 1:20).
2. Prepare the appropriate amount of reaction mix at room temperature.
   10× Buffer (20 mM Tris pH 7.4/0.1 M NaCl/1 mM DTT final)
   0.1M MnCl$_2$ (5 mM final)
   pEY substrate (75 μg/ml)
   ATP/[$^{33}$P]ATP (2.5 μM/1 μCi final)
   BSA (500 μg/ml final)
3. Add 51 μl of the diluted inhibitor to the reaction mix. (Final volume of 5 μl in 50% DMSO) Positive control wells—add blank DMSO (50%).
4. Add 35 μl of the reaction mix to each well of a 96 well plate.
5. Dilute enzyme (1:44) into enzyme dilution buffer (keep at 4° C.). Final enzyme conc.=0.22 nM.
6. Add 10 μl of the diluted enzyme to each well and mix. Negative control wells—add 10 μl 0.5 M EDTA per well instead (final 100 mM).
7. Incubate at room temperature for 30 minutes.
8. Stop by the addition of an equal volume (50 μl) of 30% TCA/0.1M Na pyrophosphate.
9. Incubate for 15 minutes to allow precipitation.
10. Transfer to Millipore filter plate.
11. Wash 3× with 15% TCA/0.1M Na pyrophosphate (125 μl per wash).
12. Allow to dry under vacuum for 2–3 minutes.
13. Dry in hood for ~20 minutes.
14. Assemble Wallac Millipore adapter and add 50 μl of scintillant to each well and count.

FLT-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:
1. Inhibitors were diluted to account for the final dilution in the assay, 1:20.
2. The appropriate amount of reaction mix was prepared at room temperature:
   10× Buffer (20 mM Tris pH 7.4/0.1 M NaCl/1 mM DTT final)
   0.1M MnCl$_2$ (5 mM final)
   pEY substrate (75 μg/mL)
   ATP/[$^{33}$P]ATP (2.5 μM/1 μCi final)
   BSA (500 μg/mL final).
3. 5 μL of the diluted inhibitor was added to the reaction mix. (Final volume of 5 μL in 50% DMSO). To the positive control wells, blank DMSO (50%) was added.
4. 35 μL of the reaction mix was added to each well of a 96 well plate.
5. Enzyme was diluted into enzyme dilution buffer (kept at 4° C.).
6. 10 μL of the diluted enzyme was added to each well and mix (5 nM final).
   To the negative control wells, 10 μL 0.5 M EDTA was added per well instead (final 100 mM).
7. Incubation was then carried out at room temperature for 30 minutes.
8. Stopped by the addition of an equal volume (50 μL) of 30% TCA/0.1M Na pyrophosphate.
9. Incubation was then carried out for 15 minutes to allow precipitation.
10. Transfered to Millipore filter plate.
11. Washed 3× with 15% TCA/0.1M Na pyrophosphate (125 μL per wash).
12. Allowed to dry under vacuum for 2–3 minutes.
13. Dryed in hood for ~20 minutes.
14. Assembled Wallac Millipore adapter and added 50 μL of scintillant to each well and counted.

What is claimed is:
1. A compound selected from
   4-(2-Phenyl-1H-imidazol-1-yl)-N-pyridin-4-ylpyrimidin-2-amine;
   4-(2-Phenyl-1H-imidazol-1-yl)-N-pyrimidin-4-ylpyrimidin-2-amine;
   4-(2-Phenyl-1H-imidazol-1-yl)-N-pyrimidin-2-ylpyrimidin-2-amine;
   4-(2-Phenyl-1H-imidazol-1-yl)-N-pyrazin-2-ylpyrimidin-2-amine;
   4-(2-Phenyl-1H-imidazol-1-yl)-N-(1,3,4-thiadiazol-2-yl)pyrimidin-2-amine;
   N-(5-Methyl-1,3,4-thiadiazol-2-yl)-4-(2-phenyl-1H-imidazol-1-yl)pyrimidin-2-amine;
   N-Isoxazol-3-yl-4-(2-phenyl-1H-imidazol-1-yl)pyrimidin-2-amine;
   N-(3-Methylisoxazol-5-yl)-4-(2-phenyl-1H-imidazol-1-yl)pyrimidin-2-amine;
   N-(4-Methyl-1,3-thiazol-2-yl)-4-(2-phenyl-1H-imidazol-1-yl)pyrimidin-2-amine;
   N-(2-Methylpyridin-4-yl)-4-(2-phenyl-1H-imidazol-1-yl)pyrimidin-2-amine;
   N-(2,6-Dimethylpyridin-4-yl)-4-(2-phenyl-1H-imidazol-1-yl)pyrimidin-2-amine;
   4-(2-Phenyl-1H-imidazol-1-yl)-N-pyridin-3-ylpyrimidin-2-amine;
   N-(1-Oxidopyndin-3-yl)-4-(2-phenyl-1H-imidazol-1-yl)pyrimidin-2-amine;

N-[3-Methoxy-5-(trifluoromethyl)phenyl]-4-(2-phenyl-1H-imidazol-1-yl)pyrimidin-2-amine;

(3-Methyl-5-{[4-(2-phenyl-1H-imidazol-1-yl)pyrimidin-2-yl]amino}phenyl)methanol;

N-{3-[(4-Acetylpiperazin-1-yl)methyl]-5-methylphenyl}-4-(2-phenyl-1H-imidazol-1-yl)pyrimidin-2-amine;

N-(3,5-Dimethylphenyl)-4-(2-pyridin-2-yl-1H-imidazol-1-yl)pyrimidin-2-amine;

N-(3,5-Dimethylphenyl)-4-(2-pyrimidin-5-yl-1H-imidazol-1-yl)pyrimidin-2-amine;

N-(3,5-Dimethylphenyl)-4-(2-pyridin-3-yl-1H-imidazol-1-yl)pyrimidin-2-amine;

4-(2-Cyclopropyl-1H-imidazol-1-yl)-N-(3,5-dimethylphenyl)pyrimidin-2-amine;

N-(3,5-Dimethylphenyl)-4-(4-methyl-2-phenyl-1H-imidazol-1-yl)pyrimidin-2-amine;

1-{2-[(3,5-Dimethylphenyl)amino]pyrimidin-4-yl}-1H-imidazole-2-carbonitrile;

N-(3,5-Dimethylphenyl)-4-(2-methyl-1H-imidazol-1-yl)pyrimidin-2-amine;

4-(2-Amino-1H-imidazol-1-yl)-N-(3,5-dimethylphenyl)pyrimidin-2-amine;

N-(2-methylphenyl)-4-(2-phenyl-1H-imidazol-1-yl)pyrimidin-2-amine;

N-(2-methoxyphenyl)-4-(2-phenyl-1H-imidazol-1-yl)pyrimidin-2-amine;

N-(2-fluorophenyl)-4-(2-phenyl-1H-imidazol-1-yl)pyrimidin-2-amine;

N-(3-chlorophenyl)-4-(2-phenyl-1H-imidazol-1-yl)pyrimidin-2-amine;

N-(3,5-dichlorophenyl)-4-(2-phenyl-1H-imidazol-1-yl)pyrimidin-2-amine;

N-(3-fluorophenyl)-4-(2-phenyl-1H-imidazol-1-yl)pyrimidin-2-amine;

N-(3-methoxyphenyl)-4-(2-phenyl-1H-imidazol-1-yl)pyrimidin-2-amine;

N-(3-methylphenyl)-4-(2-phenyl-1H-imidazol-1-yl)pyrimidin-2-amine;

N-(3,5-dimethoxyphenyl)-4-(2-phenyl-1H-imidazol-1-yl)pyrimidin-2-amine;

N-(4-chlorophenyl)-4-(2-phenyl-1H-imidazol-1-yl)pyrimidin-2-amine;

N-(4-fluorophenyl)-4-(2-phenyl-1H-imidazol-1-yl)pyrimidin-2-amine;

N-(4-methoxyphenyl)-4-(2-phenyl-1H-imidazol-1-yl)pyrimidin-2-amine;

N-(4-methylphenyl)-4-(2-phenyl-1H-imidazol-1-yl)pyrimidin-2-amine;

N-[3,5-bis(trifluoromethyl)phenyl]-4-(2-phenyl-1H-imidazol-1-yl)pyrimidin-2-amine;

N-[3-methyl-5-(trifluoromethyl)phenyl]-4-(2-phenyl-1H-imidazol-1-yl)pyrimidin-2-amine;

N-(3,5-difluorophenyl)-4-(2-phenyl-1H-imidazol-1-yl)pyrimidin-2-amine;

4-(2-phenyl-1H-imidazol-1-yl)-N-[3-(trifluoromethyl)phenyl]pyrimidin-2-amine;

N-(3,5-dimethylphenyl)-4-(2-phenyl-1H-imidazol-1-yl)pyrimidin-2-amine;

4-(2-Phenyl-1H-imidazol-1-yl)-N-pyridin-2-ylpyrimidin-2-amine;

N-{3-[(4-acetylpiperazin-1-yl)methyl]phenyl}-4-(2-phenyl-1H-imidazol-1-yl)pyrimidin-2-amine;

4-(2-Chloro-1H-imidazol-1-yl)-N-(3,5-dimethylphenyl)pyrimidin-2-amine;

N-(3,5-Dimethylphenyl)-4-[2-(3-fluorophenyl)-1H-imidazol-1-yl]pyrimidin-2-amine;

or a pharmaceutically acceptable salts thereof.

2. The compound according to claim 1 which is

N-[3-methyl-5-(trifluoromethyl)phenyl]-4-(2-phenyl-1H-imidazol-1-yl)pyrimidin-2-amine;

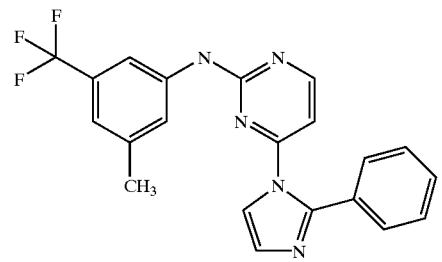

or a pharmaceutically acceptable salt thereof.

3. The compound according to claim 1 which is

N-(3,5-dimethylphenyl)-4-(2-phenyl-1H-imidazol-1-yl)pyrimidin-2-amine;

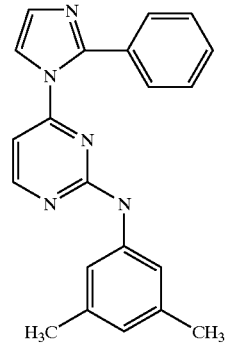

or a pharmaceutically acceptable salts thereof.

4. The compound according to claim 1 which is

N-(3-chlorophenyl)-4-(2-phenyl-1H-imidazol-1-yl)pyrimidin-2-amine;

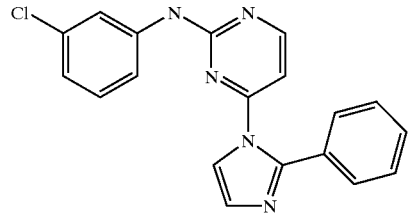

or a pharmaceutically acceptable salt thereof.

5. The compound according to claim 1 which is

N-(3,5-dimethoxyphenyl)-2-(2-phenyl-1H-imidazol-1-yl)pyrimidin-2-amine;

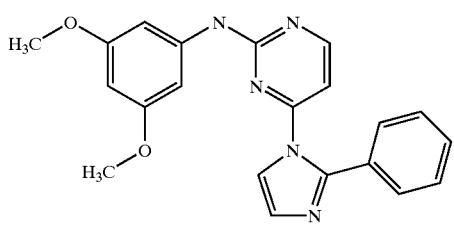

or a pharmaceutically acceptable salts thereof.

6. The compound according to claim 1 which is
4-(2-phenyl-1H-imidazol-1-yl)-N-[3-(trifluoromethyl)phenyl]pyrimidin-2-amine;

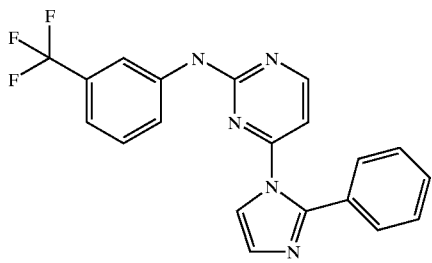

or a pharmaceutically acceptable salt thereof.

7. The compound according to claim 1 which is
(3-methyl-5-{[4-(2-phenyl-1H-imidazol-1-yl)pyrimidin-2-yl]amino}phenyl)methanol;

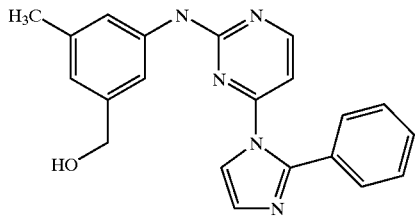

or a pharmaceutically acceptable salt thereof.

8. A pharmaceutical composition which is comprised of a compound in accordance with claim 1 and a pharmaceutically acceptable carrier.

9. A method of treating breast cancer in a mammal in need of such treatment which is comprised of administering to said mammal a therapeutically effective amount of a compound of claim 1.

10. The composition of claim 8 further comprising a second compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

11. The composition of claim 10, wherein the second compound is another angiogenesis inhibitor selected from the group consisting of a tyrosine kinase inhibitor, an inhibitor of epidermal-derived growth factor, an inhibitor of fibroblast-derive growth factor, an inhibitor of platelet derived growth factor, an MMP inhibitor, an integrin bloc er, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF.

12. The composition of claim 10, wherein the second compound is an estrogen receptor modulator selected from tamoxifen and raloxifene.

* * * * *